US012778960B2

(12) United States Patent
Hung

(10) Patent No.: US 12,778,960 B2
(45) Date of Patent: Nov. 3, 2026

(54) METHOD OF INHIBITING LIPOGENESIS WITH UBIQUITIN-SPECIFIC PEPTIDASE 24 INHIBITOR COMPOSITION

(71) Applicant: NATIONAL CHENG KUNG UNIVERSITY, Tainan City (TW)

(72) Inventor: Chien-Chung Hung, Tainan City (TW)

(73) Assignee: NATIONAL CHENG KUNG UNIVERSITY, Tainan City (TW)

(*) Notice: Subject to any disclaimer, the term of this patent is extended or adjusted under 35 U.S.C. 154(b) by 445 days.

(21) Appl. No.: 18/498,472

(22) Filed: Oct. 31, 2023

(65) Prior Publication Data

US 2024/0197749 A1 Jun. 20, 2024

(30) Foreign Application Priority Data

Nov. 25, 2022 (TW) .................................. 111145277

(51) Int. Cl.
*A61K 31/5415* (2006.01)
*A61P 3/06* (2006.01)

(52) U.S. Cl.
CPC ............ *A61K 31/5415* (2013.01); *A61P 3/06* (2018.01)

(58) Field of Classification Search
CPC .................................................. A61K 31/5415
USPC .......................................................... 514/225
See application file for complete search history.

(56) References Cited

U.S. PATENT DOCUMENTS

| | | | | |
|---|---|---|---|---|
| 11,827,611 | B2 * | 11/2023 | Hung | C07C 49/825 |
| 11,993,775 | B2 * | 5/2024 | Hung | A61K 31/18 |
| 2022/0024887 | A1 * | 1/2022 | Hung | C07C 49/825 |
| 2022/0025375 | A1 * | 1/2022 | Hung | A61K 31/18 |

FOREIGN PATENT DOCUMENTS

| | | | | |
|---|---|---|---|---|
| DE | 1120451 B | * 12/1961 | | C07D 279/28 |
| TW | 202203933 A | 2/2022 | | |

OTHER PUBLICATIONS

DE1120451B English Translation, Google Patents, 1961, pp. 1-4 (Year: 1961).*

Jiang et al., "CRISPR-Cas: New Tools for Genetic Manipulations from Bacterial Immunity Systems", Jul. 22, 2015, vol. 69, Annual reviews, 23 pages.

Hsu et al., "Development and Applications of CRISPR-Cas9 for Genome Engineering", Feb. 27, 2015, HHS Public Access, 34 pages.

Sun et al., "Isoflavonoids from Crotalaria albida Inhibit Adipocyte Differentiation and Lipid Accumulation in 3T3-L1 Cells via Suppression of PPAR-γ Pathway", Aug. 18, 2015, pp. 1-13, PLOS ONE.

O'Commell et al., "Programmable RNA recognition and cleavage by CRISPR/Cas9", Jun. 11, 2015, HHS Public Access, 23 pages.

Darlington et al., "The Role of C/EBP Genes in Adipocyte Differentiation", Nov. 13, 1998, pp. 30057-30060, vol. 46, The Journal of Biological Chemistry.

Wang et al., "USP24 promotes drug resistance during cancer therapy", Mar. 25, 2021, Cell Death & Differentiation, 19 pages.

* cited by examiner

*Primary Examiner* — Jeffrey H Murray
*Assistant Examiner* — Rilla Marie Samsell
(74) *Attorney, Agent, or Firm* — MCBEE MOORE & VANIK IP, LLC

(57) ABSTRACT

The present invention relates to a method of inhibiting lipogenesis with a ubiquitin-specific peptidase 24 (USP24) inhibitor composition. The USP24 inhibitor composition, which includes a carbonyl substituted phenyl compound, can specifically inhibit lipogenesis and hepatic lipid accumulation in a high-fat individual, thereby being applied to a method of inhibiting lipogenesis and hepatic lipid accumulation in a high-fat subject.

7 Claims, 28 Drawing Sheets

Specification includes a Sequence Listing.

SEQUENCE LISTING

```
Sequence total quantity: 5
SEQ ID NO: 1           moltype = DNA  length = 42
FEATURE                Location/Qualifiers
source                 1..42
                       mol_type = other DNA
                       organism = synthetic construct
SEQUENCE: 1
acggtggcgc cactgcttac atgaatgcag tgttccagca gc                     42

SEQ ID NO: 2           moltype = DNA  length = 20
FEATURE                Location/Qualifiers
source                 1..20
                       mol_type = other DNA
                       organism = synthetic construct
SEQUENCE: 2
tggctgttgt ggaagtgtgc                                              20

SEQ ID NO: 3           moltype = DNA  length = 20
FEATURE                Location/Qualifiers
source                 1..20
                       mol_type = other DNA
                       organism = synthetic construct
SEQUENCE: 3
gcctgctact ccacaagttg                                              20

SEQ ID NO: 4           moltype = DNA  length = 475
FEATURE                Location/Qualifiers
misc_feature           1..475
                       gene = USP24
source                 1..475
                       mol_type = other DNA
                       organism = Mus musculus
SEQUENCE: 4
tggctgttgt ggaagtgtgc tatggtagaa tactcattgt cctccccact gtttctgttc  60
ctttttttccc agtacctgcc cccggtggat agcaggtcca gctcagggtt tgtggggctg  120
aggaacggtg gcgctacttg ttacatgaat gcggtcttcc agcagctgta tatgcagccc  180
gggcttccgg aggtgagcgc ttcctcctct cctgtttggc atgcttaatt attattgcct  240
ctgcttgtag ctatagttaa aaattcttta ttagcttctg aaatctgcaa agatgttata  300
gtcacacatg tctgtaaatc tattctttta atcagtaatt tgaccaaatg taatttttat  360
acatacaaaa ttaattctca agctatttta tgaagttgta cttaatattt tagactatct  420
ggctctattt tcagcacatc ttattaacac agtcacaact tgtggagtag caggc       475

SEQ ID NO: 5           moltype = DNA  length = 475
FEATURE                Location/Qualifiers
misc_feature           1..475
                       product = USP24 knock out gene
source                 1..475
                       mol_type = other DNA
                       organism = Mus musculus
SEQUENCE: 5
tggctgttgt ggaagtgtgc tatggtagaa tactcattgt cctccccact gtttctgttc  60
ctttttttccc agtacctgcc cccggtggat agcaggtcca gctcagggtt tgtggggctg  120
aggaacggtg gcgccactgc ttacatgaat gcagtgttcc agcagctgta tatgcagccc  180
gggcttccgg aggtgagcgc ttcctcctct cctgtttggc atgcttaatt attattgcct  240
ctgcttgtag ctatagttaa aaattcttta ttagcttctg aaatctgcaa agatgttata  300
gtcacacatg tctgtaaatc tattctttta atcagtaatt tgaccaaatg taatttttat  360
acatacaaaa ttaattctca agctatttta tgaagttgta cttaatattt tagactatct  420
ggctctattt tcagcacatc ttattaacac agtcacaact tgtggagtag caggc       475
```

METHOD OF INHIBITING LIPOGENESIS WITH UBIQUITIN-SPECIFIC PEPTIDASE 24 INHIBITOR COMPOSITION

RELATED APPLICATION

This application claims priority to Taiwan Application Serial Number 111145277, filed Nov. 25, 2022, which is herein incorporated by reference in its entirety.

BACKGROUND

The Sequence Listing XML associated with this application is filed in electronic format via EFS-Web and is hereby incorporated by reference into the specification in its entirety. The file name of the Sequence Listing XML is "SP-5836-US_SEQ_LIST.xml", created on Oct. 11, 2023, with a file size of 7,254 bytes.

Field of Invention

The present invention relates to a method of using ubiquitin-specific peptidase (USP) 24 inhibitor composition. More specifically, the present invention relates to a method of inhibiting lipogenesis with USP 24 inhibitor composition.

Description of Related Art

Ubiquitin-Specific Peptidase 24 (USP24) is a deubiquitinase (DUB) enzyme that regulates the stability of its substrate proteins by removing ubiquitin molecules. Previous studies have shown that USP24 can stabilize various proteins associated with cancer progression, such as p53, mouse double minute 2 homolog (MDM2), transcription factor E2F4 (E2F4), discoidin domain receptor 2 (DDR2) and the like. Additionally, previous researchs by the inventors have demonstrated that USP24 is related to cancer worsening and drug resistance. The activity inhibited by USP24 with USP24 inhibitors can delay or reverse multiple drug resistance in cancer.

However, there is still lack of research on the other aspects of USP24 inhibitors. There is an urgent need to develope different applications for USP24 inhibitors.

SUMMARY

Accordingly, an aspect of the present invention provides a method of inhibiting lipogenesis with a ubiquitin-specific peptidase (USP) 24 inhibitor composition, and the USP 24 inhibitor composition includes carbonyl-substituted phenyl compound and/or its salt as active ingredients, thereby inhibiting lipid lipogenesis.

Moreover, another aspect of the invention provides a method of inhibiting hepatic lipid accumulation with a USP 24 inhibitor composition, and the USP 24 inhibitor composition includes carbonyl-substituted phenyl compound and/or its salt as active ingredients, thereby reducing hepatic lipid accumulation.

Furthermore, yet another embodiment of the invention provides a method of inhibiting the expression of PPAR-γ and/or PLIN1 genes with a USP 24 inhibitor composition, and the USP 24 inhibitor composition includes carbonyl-substituted phenyl compound and/or its salt as active ingredients, thereby reducing the expression levels of SREBP1 and/or PPARγ.

According to the aforementioned aspect of the present invention, a method of inhibiting lipogenesis with a USP 24 inhibitor composition is provided. In one embodiment, the USP 24 inhibitor composition can include, as an active ingredient, carbonyl-substituted phenyl compound and/or its salt as represented by formula (I):

(I)

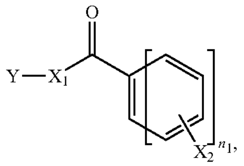

in formula (I), $X_1$ represents a single bond or NH, $n_1$ represents an integer of 1 or 2, Y represents a monovalent group, and $X_2$ represents a hydrogen atom or hydroxy group. The salts of carbonyl-substituted phenyl compound can include, but be not limited to, oxalates, phosphates, sulfates, and hydrochlorides.

In the aforementioned embodiment, when $X_1$ represents a single bond, $n_1$ is the integer 1, in formula (I-1), $R_1$ represents an alkyl piperazine group as shown in formula (I-2), where # represents the connection point with the nitrogen atom of the thiazole group (I-1), and $n_2$ represents an integer from 1 to 4:

(I-1)

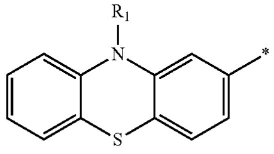

(I-2)

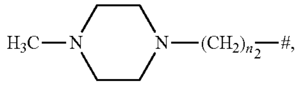

or when $X_1$ represents NH, $n_1$ is the integer 2, and as shown in formula (I-4), in which ** represents the connection point with the carbonyl group:

(I-4)

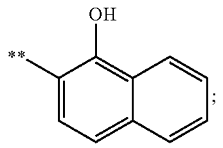

in which, when $X_2$ represents a hydrogen atom, Y represents a monovalent group having a thiazole group as shown in formula (I-1), and * in formula (I-1) represents the connection point with $X_1$, or when $X_2$ represents a hydroxy group, Y represents a monovalent group having a nitrophenylsulfonylamino group as shown in formula (I-5), * in formula (I-5) represents the connection point with $X_1$, $X_1$ represents NH, and $R_2$ in formula (I-5) represents butyl:

(I-1)

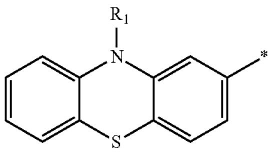

(I-5)

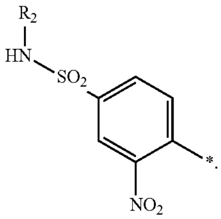

In the aforementioned embodiment, the carbonyl-substituted phenyl compound can have structures as shown in formula (I-3-1), formula (I-3-2), or formula (I-3-3):

(I-3-1)

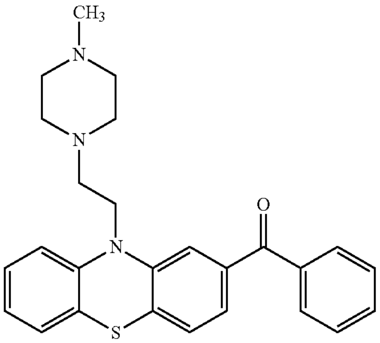

(I-3-2)

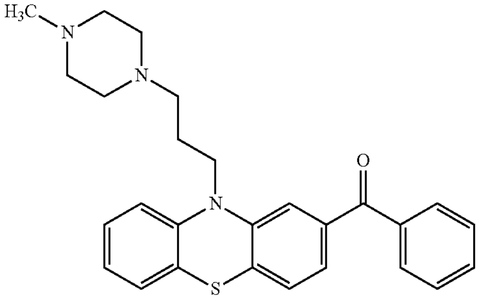

(I-3-3)

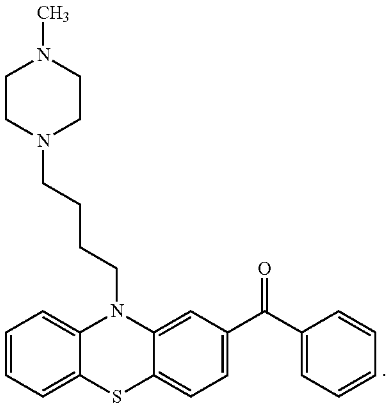

In the aforementioned embodiment, the aforementioned carbonyl-substituted phenyl compound has a structure as shown in formula (I-6):

(I-6)

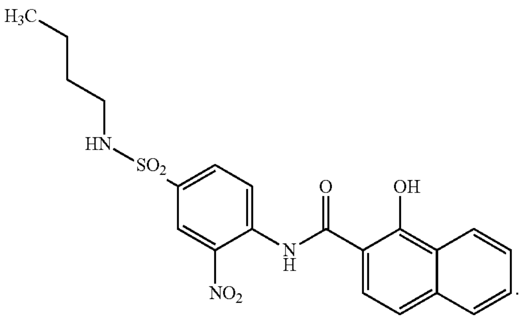

In the aforementioned embodiment, the aforementioned pharmaceutical composition can optionally include a pharmaceutically acceptable carrier.

In the aforementioned embodiment, the pharmaceutical composition mentioned above can be administered to a subject in vitro, and this subject can be, for example, adipocytes, preadipocytes, and/or adipocyte-like cells. In some examples, the effective in vitro dose of the carbonyl-substituted phenyl compound administered to the subject can be in a range of 1 μM to 20 μM.

According to another embodiment of the present invention, a inhibiting hepatic lipid accumulation with a USP 24 inhibitor composition is provided. In one embodiment, the aforementioned USP 24 inhibitor composition can include a carbonyl-substituted phenyl compound and/or its salt as represented by formula (I) as an active ingredient, in which the effective dose of the carbonyl-substituted phenyl compound administered to the subject can be in a range, for example, of 5 mg/kg body weight to 20 mg/kg body weight.

In the aforementioned embodiment, the subject has hyperlipidemia. In one example, the subject can be mice, for example.

According to another embodiment of the present invention, a method of inhibiting the expression of PPAR-γ and/or PLIN1 genes with a USP 24 inhibitor composition is provided. In one embodiment, the USP 24 inhibitor composition can include a carbonyl-substituted phenyl compound and/or its salt as shown in formula (I-3-1) as active ingredients, thereby reducing the expression levels of SREBP1 and/or PPARγ.

With application to the USP24 inhibitor composition of the present invention, which includes the carbonyl-substituted phenyl compound, can specifically inhibit lipogenesis and hepatic lipid accumulation in a subject with hyperlipidemia, and can thus be applied in preparation of a medicinal composition for inhibiting lipogenesis.

It is to be understood that both the foregoing general description and the following detailed description are by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1A:
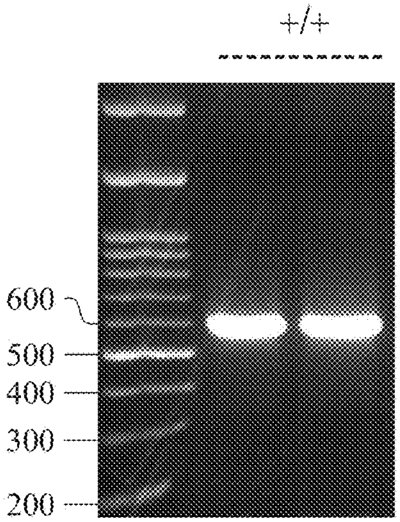
FIG. 1A and FIG. 1B show the DNA agarose gel electrophoresis results of the USP24 gene typing in experimental animals according to one embodiment of the present invention.

With reference to the accompanying drawings, the following detailed description provides examples of the present invention. If a term defined or used in a reference is inconsistent or opposite as it is defined or used in the drawings and the specification, the definition of the term herein, other than that in the reference, is preferably applicable.

As aforementioned, the present invention provides a method of inhibiting lipogenesis with a ubiquitin-specific peptidase (USP) 24 inhibitor composition. This USP 24 inhibitor composition can include a carbonyl-substituted phenyl compound and/or its salt as active ingredients, thereby inhibiting lipogenesis.

Specifically, the USP24 inhibitor composition can include carbonyl-substituted phenyl compound and/or its salt. In one embodiment, the aforementioned carbonyl-substituted phenyl compound has a structure as represented by formula (I):

(I)

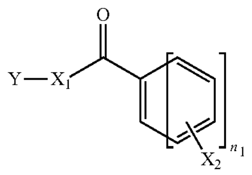

in the embodiment of the formula (I), $X_1$ represents a single bond or NH, $n_1$ represents an integer of 1 or 2, Y represents a monovalent group, and $X_2$ represents a hydrogen atom or hydroxy group.

In an example of the formula (I-1), when $X_1$ represents a single bond, $n_1$ is the integer 1, $X_2$ represents a hydroxy group, Y represents a monovalent group having a thiazole group as shown in formula (I-1), and * in formula (I-1) represents the connection point with $X_1$:

(I-1)

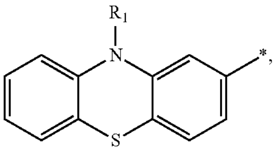

in formula (I-1), $R_1$ represents an alkyl piperazine group as shown in formula (I-2), where # represents the connection point with the nitrogen atom of the thiazole group (I-1), and n2 represents an integer from 1 to 4:

(I-2)

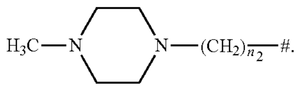

In the above example, the alkyl piperazine group as shown in formula (I-2) has a structure as shown in formula (I-2-1, for example, NCI677-08, also known as USP24-i101), formula (I-2-2), or formula (I-2-3, for example, NCI677397, also known as USP24-i1):

(I-2-1)

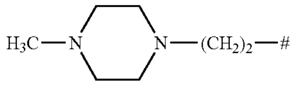

(I-2)

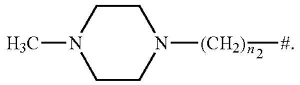

(I-2-3)

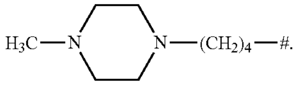

In the above example, the carbonyl-substituted phenyl compound has a structure as shown in formula (I-3-1, for example, NCI677-08, also referred to as USP24i, USP24-i, USP24-i-a or USP24-i101), formula (I-3-2), or formula (I-3-3, for example, NCI677397, also referred to as USP24-i1):

(I-3-1)

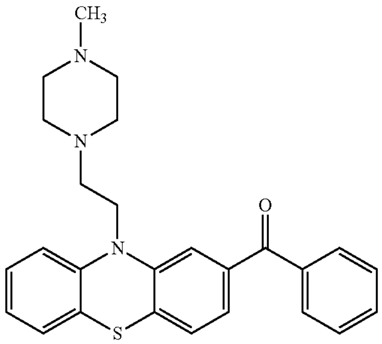

(I-3-2)

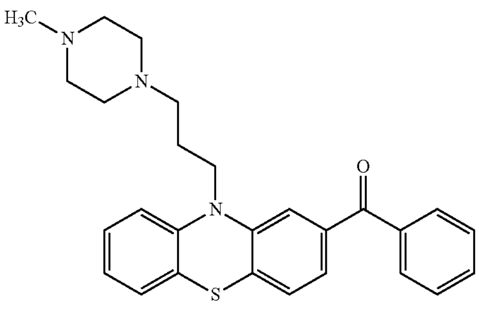

-continued (I-3-3)

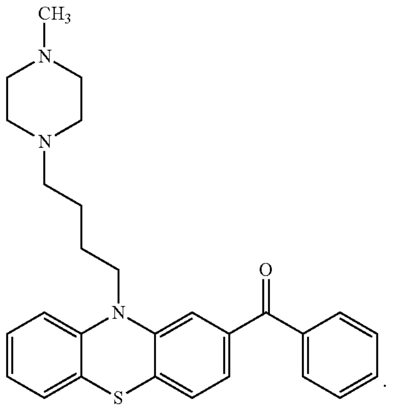

In another example, $X_1$ represents NH, $n_1$ is the integer 2 of the thiazole group as shown in formula (I-1), and as shown in formula (I-4), in which ** represents the connection point with the carbonyl group, $X_2$ represents a hydrogen atom, Y represents a monovalent group having a nitrophenylsulfonylamino group as shown in formula (I-5), * in formula (I-5) represents the connection point with nitrogen atom, and R2 represents the connection point with butyl group:

(I-4)

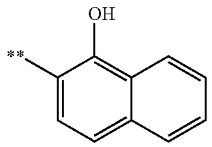

(I-5)

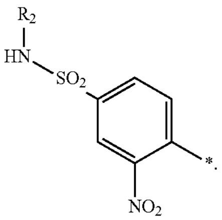

In the aforementioned examples, the aforementioned carbonyl-substituted phenyl compound has a structure as shown in formula (I-6):

(I-6)

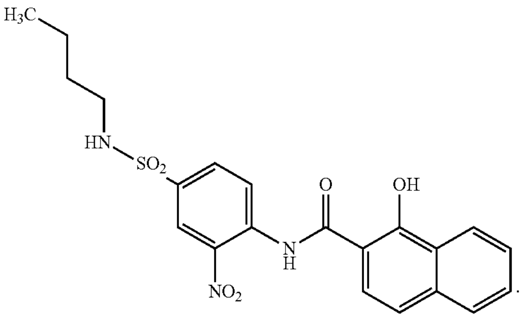

Regarding the preparation of the aforementioned USP24 inhibitor, please referred to Taiwan Patent Application No.

110104339, which is herein incorporated by reference. The carbonyl-substituted phenyl compound of the present invention can be converted into pharmaceutically acceptable salts, and these salts can be converted into free alkaline compounds using conventional methods. The carbonyl-substituted phenyl compound of the present invention, whether in the form of free alkalines or pharmaceutically acceptable salts, can exhibit therapeutic effects, depending on the desired properties such as solubility, dissolution, hygroscopicity, and pharmacokinetics. Specific examples of pharmaceutically acceptable salts as aforementioned include salts formed with inorganic acids, such as hydrochloric acid, trifluoroacetic acid, propionic acid, oxalic acid, malic acid, succinic acid, fumaric acid, maleic acid, lactic acid, citric acid, ethanesulfonic acid, aspartic acid, and glutamic acid. These salts can be methanesulfonate salts, hydrochloride salts, phosphate salts, benzenesulfonate salts, or sulfate salts. These salts can be mono-salts or di-salts. For example, methanesulfonate salts can be mono-methanesulfonate salts or dimethanesulfonate salts. The carbonyl-substituted phenyl compound of the present invention can exist in the form of hydrates or solvates. In some embodiments, the carbonyl-substituted phenyl compound or its salt can be used in a medicinal composition. There is no particular limitation on the form of the salts of the carbonyl-substituted phenyl compound of the present invention; however, in some embodiments, the salts of these compounds can include, but be not limited to, oxalate salts, phosphate salts, sulfate salts, and hydrochloride salts, depending on actual requirements.

In the examples, the aforementioned USP24 inhibitor can inhibit lipogenesis in test subject for use in the preparation of a medicinal composition that inhibit lipogenesis.

The term "inhibition of lipogenesis" referred herein means the specific reduction of lipid droplets and the gene expression of PPAR-γ (peroxisome proliferator-activated receptor-γ) and PLIN1 (Perilipin 1) in adipocytes, thereby decreasing the expression levels of SREBP1 (sterol regulatory element-binding protein 1), PPAR-γ, and C/EBPβ (CCAAT/enhancer binding protein β). This inhibition disrupts lipogenesis and reduces the formation of adipocytes. On the other hand, inhibition of lipogenesis can prevent the accumulation of lipids in the liver, reduce the intake of free fatty acids, improve liver function (such as reducing liver index and total cholesterol index), thereby reducing lipid accumulation in the liver or even losing body weight.

In some examples, the aforementioned test subject can be in vitro cells, including but not limited to adipocytes, pre-adipocytes (also known as adipocyte progenitor cells), and/or adipocyte-like cells, rather than limiting to those aforementioned. In other examples, the aforementioned test subject can also be a living organism (in vivo), such as a mammalian animal.

When evaluating the effects of USP24 inhibitor, the USP24 gene of the test subject (e.g., in vitro cells) can be either normal (e.g., wild-type) or knocked out, and these cells can be induced to differentiate into adipocytes using differentiation medium. In the case of living organisms (e.g., in vivo), the USP24 gene of the subjects can be either normal (e.g., wild-type) or knocked out, and they can be fed with a normal diet (ND) or induced to hyperlipidemia through a high-fat diet (HFD), so as to assess the effectiveness of USP24 inhibitor in inhibiting lipogenesis.

Through confirmation of the various models as aforementioned, it has been demonstrated that USP24 inhibitor can indeed inhibit lipogenesis, prevent hepatic lipid accumulation, reduce lipid droplets in adipocytes, downregulate the gene expression of PPAR-γ and PLIN1, and improve liver function. This leads to a reduction in adipocyte formation, thereby reducing lipid accumulation in the liver and losing body weight.

In one embodiment, the aforementioned pharmaceutical composition can be optionally added with a pharmaceutically acceptable carrier. This pharmaceutical composition can be administered to cancer cells or individuals through conventional routes, including but not limited to intraperitoneal (i.p.), intravenous (i.v.), intramuscular (i.m.), intrathecal, cutaneous, subcutaneous (s.c.), transdermal, sublingual, buccal, rectal, vaginal, ocular, otic, nasal, inhalation, oral, nebulization, or other routes, depending on specific requirements.

In some examples, the administration of the aforementioned carbonyl-substituted phenyl compound to the test subject in vitro can be at effective doses ranging from, for instance, 1 μM to 20 μM, or 5 μM to 10 μM.

In certain specific examples, the effective dosage of the aforementioned carbonyl-substituted phenyl compound when administered to an individual can range from 5 mg/kg to 20 mg/kg, or from 5 mg/kg to 15 mg/kg, or approximately 10 mg/kg. In these examples, the individuals cam, for instance, have hyperlipidemia.

In this embodiment, there are no restrictions on the pharmaceutically acceptable carrier and/or an excipient. For example, they can be water, solutions, organic solvents, pharmaceutically acceptable oils, fats, or mixtures thereof. In some instances, a pharmaceutically acceptable carrier and/or an excipient can include physiological saline, sterile water, Ringer's solution, buffered saline, albumin injection, dextrose solution, maltodextrin solution, glycerol, ethanol, or a mixture of at least one of these, and if necessary, known additives such as antioxidants, buffers, preservatives, etc., can be added.

Generally, USP24 inhibitor can modulate target genes and/or proteins, wherein the target genes and/or proteins can be involved in reducing USP24 content, thereby inhibiting lipogenesis. Suitable target genes and/or proteins can include but be not limited to USP24, PPAR-γ, and/or PLIN1, which can disrupt lipogenesis, prevent hepatic lipid accumulation, reduce lipid droplets, downregulate the gene expression of PPAR-γ and/or PLIN1 in adipocytes, and improve liver function. This leads to a reduction in adipocyte formation, thereby reducing lipid accumulation in the liver and losing body weight.

Thereinafter, it will be understood that specific formulations, specific aspects, specific examples, specific terms and specific embodiments described hereinafter are shown by way of illustration and not as limitations of the invention. The principal features of this invention can be employed in various embodiments without departing from the scope of the invention. Thus, one skilled in the art can easily ascertain the essential characteristics of the present invention and, without departing from the spirit and scope thereof, can make various changes and modifications of the invention to adapt it to various usages and conditions.

Example 1

1.1 Cell Culture

Commercially available mouse fibroblast cell line 3T3-L1 was cultured in commercially available Dulbecco's Modified Eagle Medium (DMEM) containing 10% fetal bovine serum (FBS), 100 μg/mL streptomycin, and 100 U/ml penicillin G sodium salt. All cell cultures were maintained at 37° C. with 5% $CO_2$.

1.2 Animal Care

Animal-related experiments had been reviewed and approved by the Institutional Animal Care and Use Committee (IACUC) of National Cheng Kung University (NCKU). These genetically modified mice were generated at the National Laboratory Animal Center (NLAC) in Tainan, Taiwan. After breeding, 2 months-old wild-type mice and genetically modified mice were used to study lipogenesis progress. The cages provided adequate space, and the population density allowed the animals to move freely. The provided feed was sufficient for the normal growth and maintenance of regular body weight in both wild-type and genetically modified mice. Genetically modified mice had access to fresh, uncontaminated drinking water. Genetically modified mice were observed and cared for at least 2 to 3 times a week. All animal-related procedures were conducted in accordance with relevant guidelines and regulations.

Example 2

2.1 Establishment of USP24 Functional (Conditional) Gene Knockout (KO) Mice

In order to investigate the specificity of USP24 inhibitor, this example utilized Clustered Regularly Interspaced Short Palindromic Repeats (CRISPR)-CRISPR-associated protein 9 (Cas9) gene editing technology to establish USP24 gene knockout (KO) mice.

Based on research related to USP24, the deletion of the 1695th amino acid residue cysteine (Cys1695) in the USP24 protein could lead to enzyme inactivation. In this example, a guide RNA (gRNA) sequence, as shown in SEQ ID NO:1, was designed for use with CRISPR-Cas9 gene editing technology to mutate the 1695th amino acid residue of USP24 from cysteine to alanine (C1695A) to create USP24 functional (conditional) knockout mice.

For a comprehensive overview of the CRISPR/Cas system for gene editing, please referred to publications such as Jian W. et al. in Annu. Rev. Microbiol., Volume 69, pages 209-228 (2015); Hsu P. D. et al. in Cell, Volume 157, Issue 6, pages 1262-1278 (2014); and O'Connell M. R. et al. in Nature, Volume 516, issue 7530, pages 263-266 (2014). These references were incorporated herein by reference.

The resulting USP24 functional (conditional) KO mice had a mutation of the 1695th amino acid residue of the USP24 protein, changing cysteine to alanine (C1695A). The mutation site introduced by the gRNA corresponded to nucleotides tg (wild-type) at positions 24223-24224, as shown in GenBank Accession No. AL954352.10, and was mutated to gc (USP24 knockout mutant). Additionally, the gRNA introduced a restriction enzyme site NarI and deleted the restriction enzyme site BbsI in the USP24 gene to facilitate subsequent gene typing. The introduced NarI restriction enzyme site corresponded to nucleotides at positions 24214-24219, as shown in GenBank Accession No. AL954352.10 (altering DNA sequence without changing the original amino acid sequence), and the deleted BbsI restriction enzyme site corresponded to nucleotides at positions 24238-24243, as shown in GenBank Accession No. AL954352.10 (altering DNA sequence without changing the original amino acid sequence).

Figure 1B:
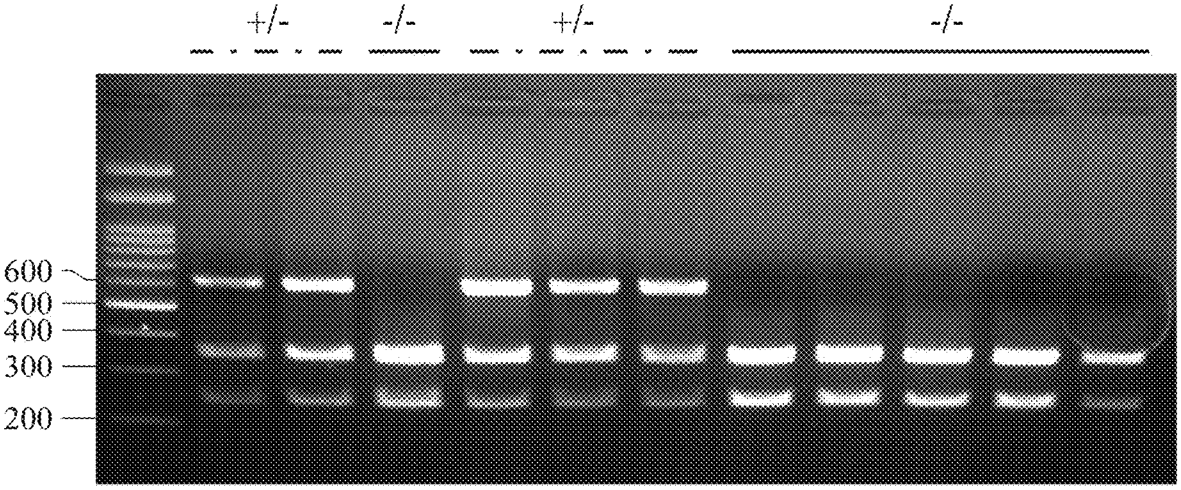

Subsequently, PCR was performed using upstream and downstream primers as shown in SEQ ID NOs:2-3, resulting in a PCR product of 475 base pairs, corresponding to nucleotides 24085-24559, as shown in GenBank Accession No. AL954352.10. Gene typing using NarI revealed the results as shown in FIG. 1A. FIGS. 1A and 1B showed the DNA agarose gel electrophoresis analysis of USP24 gene typing in experimental animals of an embodiment of the present invention, where the symbols + or − represent one of the alleles of the USP24 gene as dominant (+, i.e., wild-type, as shown in SEQ ID NO:4) or recessive (−, i.e., USP24 KO type, as shown in SEQ ID NO:5).

2.2 Gene Deletion of USP24 Suppressed Lipogenesis

USP24 wild-type (WT) mice and USP24 KO mice were fed a high-fat diet (HFD) for an extended period (19 weeks) to investigate the role of USP24 in lipogenesis. The weight of each mouse was recorded weekly (as shown in FIG. 2C), as well as blood glucose levels (as shown in FIG. 2D). After 19 weeks of either a normal diet (ND) or HFD, images were taken to document the gross appearance of the mice (as shown in the top row of FIG. 2A). Subsequently, the mice were euthanized, and major organs such as the liver, kidney, and pancreas were collected (as shown in the bottom row of FIG. 2A). Tissue sections were stained and analyzed to assess changes in lipogenesis in major organs (as shown in FIG. 2B).

Please referred to FIGS. 2A to 2D, which respectively showed the gross appearance and images (FIG. 2A) of major organs of USP24 KO mice after 19 weeks of HFD according to an embodiment of the present invention, as well as liver tissue section staining (FIG. 2B), body weight (FIG. 2C), and blood glucose levels (FIG. 2D).

Figure 2A:
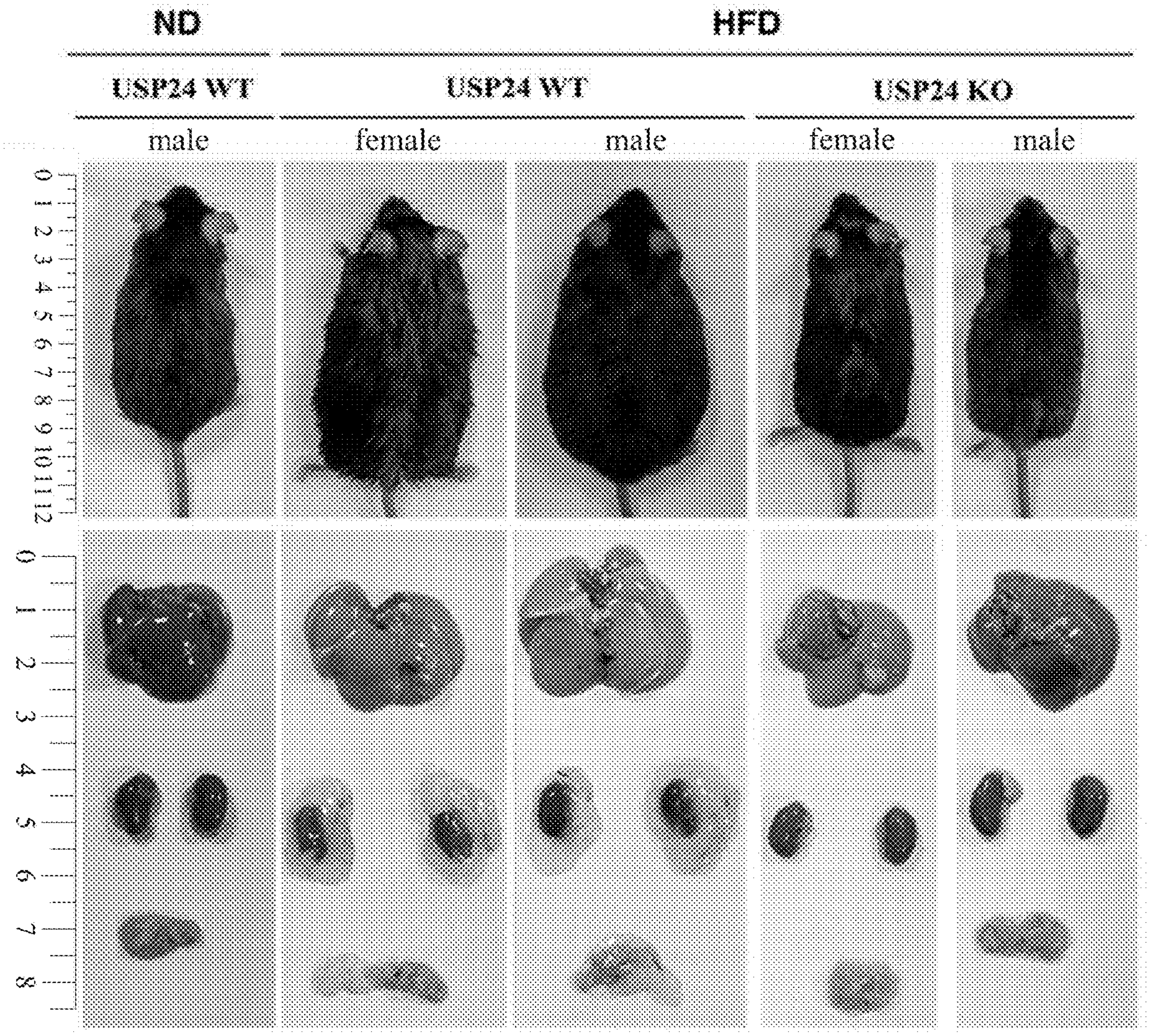
FIG. 2A, FIG. 2B, FIG. 2C, and FIG. 2D respectively show results of images (FIG. 2A) of the gross appearance and major organs, stained tissue sections (FIG. 2B) of liver, body weight (FIG. 2C), and blood glucose (FIG. 2D) of USP24 knockout (KO) mice and USP24 wild-type mice after 19 weeks of high-fat diet (HFD) according to one embodiment of the present invention.
Figure 2B:
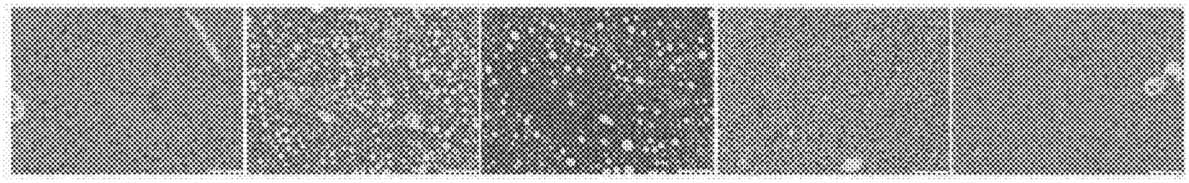
Figure 2C:
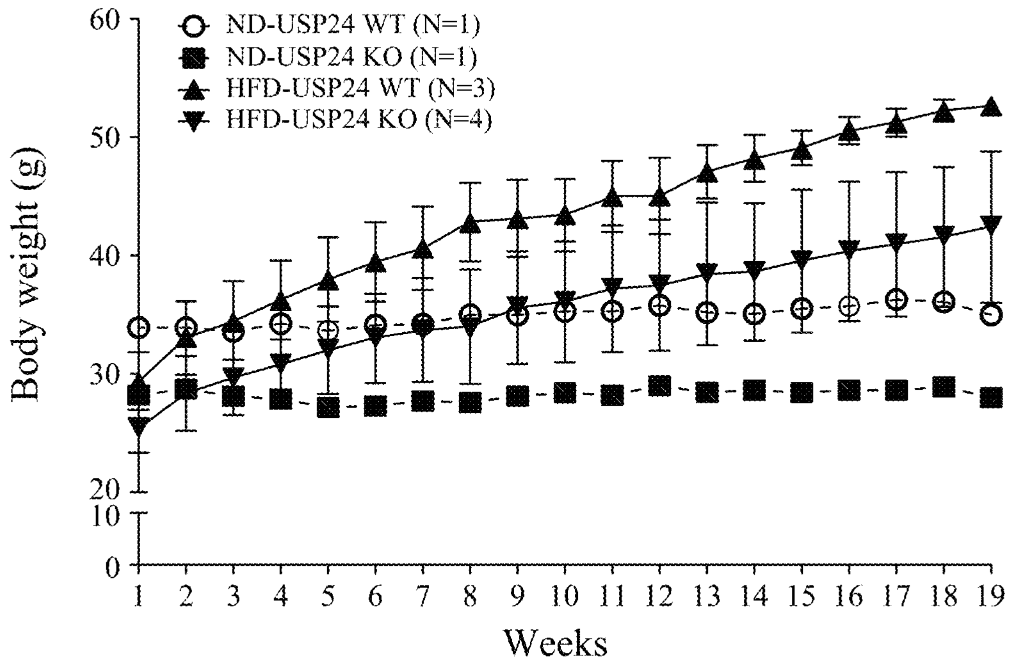
Figure 2D:
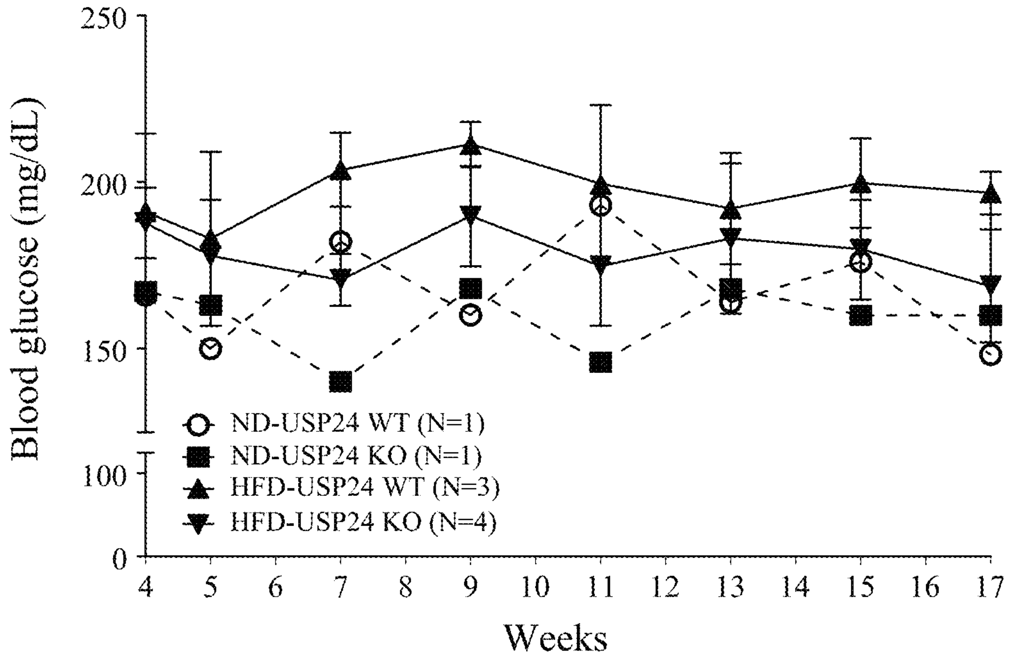

As shown in the results in FIGS. 2A and 2B, the body size of USP24-WT HFD mice was significantly larger than that of USP24-KO HFD mice, indicating that the absence of the USP24 gene in USP24-KO mice could suppress lipogenesis and potentially improve obesity induced by HFD.

Furthermore, the lipid content in USP24-WT HFD mice was significantly higher than in USP24-KO HFD mice, as indicated by vacuoles in FIG. 2B (representing lipid accumulation). Please referred to FIG. 2B, from left to right, the second and third images corresponded to liver tissue section staining of USP24-WT HFD females and males, respectively, showing the accumulation of a large number of lipid droplets (vacuoles) in the livers of USP24-WT HFD mice (vacuoles not shown). However, please referred to FIG. 2B, from left to right, the fourth and fifth images corresponded to liver tissue section staining of USP24-KO HFD females and males, respectively, and showed little to no lipid accumulation (only minimal vacuoles or none), suggesting that the loss of the USP24 gene could potentially improve fatty liver.

Moreover, as shown in the results in FIGS. 2C and 2D, after 19 weeks of ND mice (referred to as USP24-KO ND mice, N=1), the body weight of these mice was significantly lower than that of USP24 wild-type ND mice (referred to as USP24-WT ND mice, N=1) (as shown in FIG. 2C). However, there was no significant difference in blood glucose levels between the two groups (as shown in FIG. 2D), indicating that the deletion of the USP24 gene did not affect the eating habits of USP24-KO ND mice. On the other hand, after 19 weeks of HFD (referred to as USP24-KO HFD mice, N=4), their body weight and blood glucose levels were significantly lower than those of USP24 wild-type HFD mice (referred to as USP24-WT HFD mice, N=3), as shown in FIG. 2C and FIG. 2D.

Figure 3A:
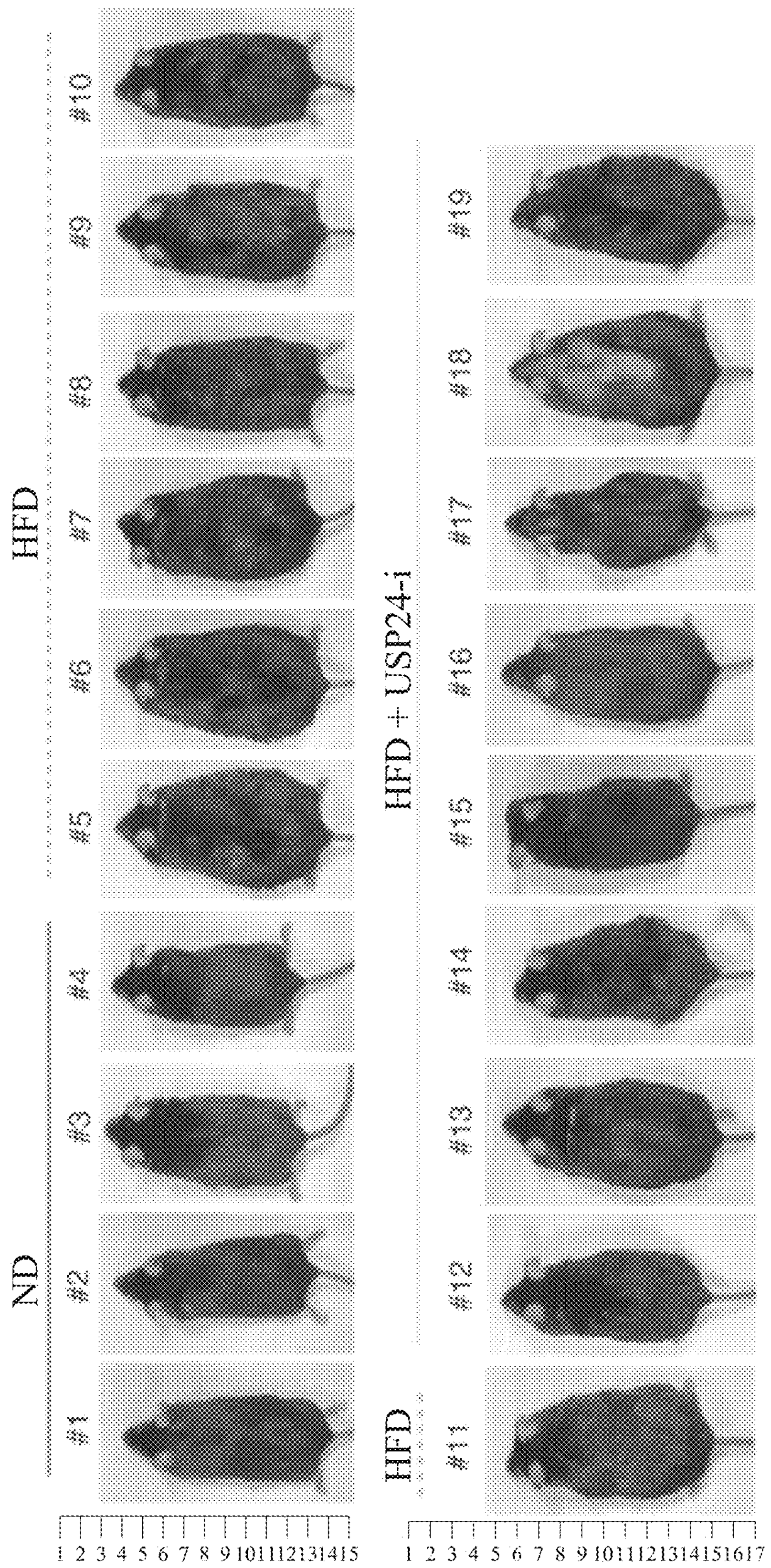
FIG. 3A and FIG. 3B depict the gross appearance (FIG. 3A) and body weight (FIG. 3B) of USP24 knockout (KO) mice and USP24 wild-type mice after 2 months of oral administration of a USP24 inhibitor according to one embodiment of the present invention.
Figure 3B:
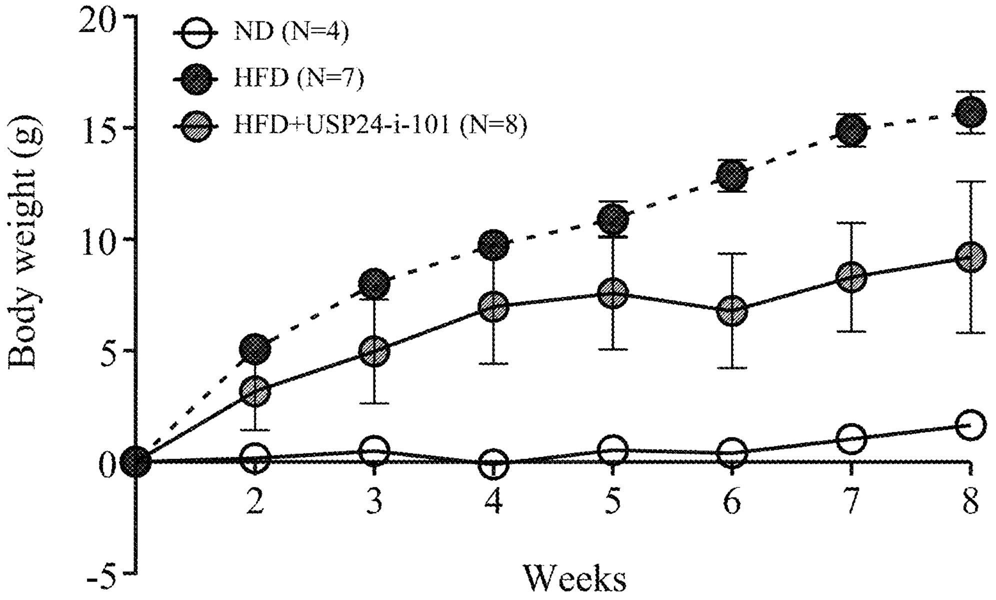

Please referred to FIGS. 3A and 3B, which depicted the gross appearance (FIG. 3A) and body weight (FIG. 3B) of USP24 KO mice and USP24 wild-type mice after 2 months of oral administration of a USP24 inhibitor according to an embodiment of the present invention.

As shown in the results in FIGS. 3A and 3B, after 2 months of oral administration of a USP24 inhibitor, all USP24-WT HFD mice had significantly higher body weights than USP24-KO HFD mice, indicating that the USP24 inhibitor could specifically target USP24 and thereby improve obesity.

2.3 USP24 Inhibitor Blocked Lipogenesis

It was known that USP24 inhibitor (USP24-i1, NCI677397, Formula I-3-3) could block USP24 catalytic activity, delaying or reversing cancer drug resistance. Please referred to FIGS. 4A and 4B, which respectively showed the results of liver tissue section H&E (hematoxylin and eosin) staining (FIG. 4A) and liver ultrasonography (FIG. 4B) after 2 months of oral administration of USP24 inhibitor in USP24 KO mice and USP24 wild-type (WT) mice following 2 months of a normal diet (ND) or high-fat diet (HFD) according to an embodiment of the present invention.

Figure 4A:
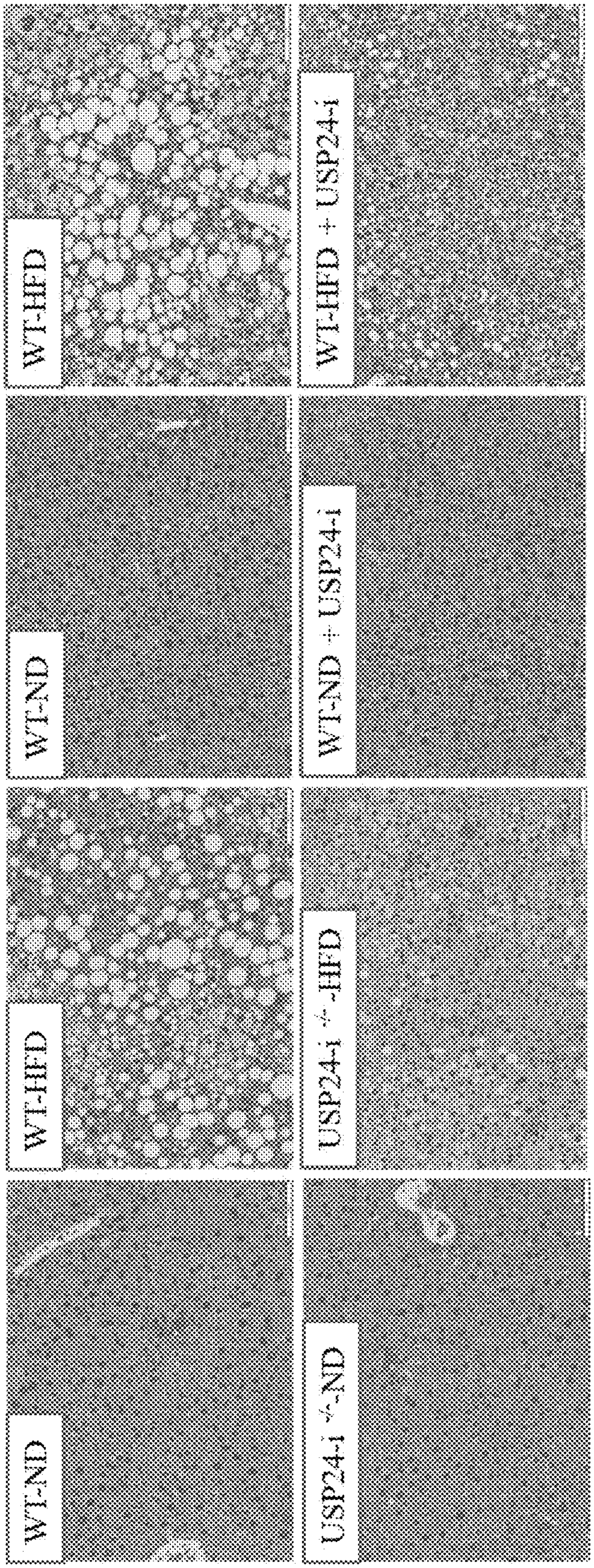
FIG. 4A and FIG. 4B respectively show results of liver tissue sections stained with H&E (FIG. 4A) and liver ultrasound examination (FIG. 4B) of USP24 knockout (KO) mice and USP24 wild-type mice after 2 months of normal diet (ND) or high-fat diet (HFD) followed by administration of a USP24 inhibitor according to one embodiment of the present invention.
Figure 4B:
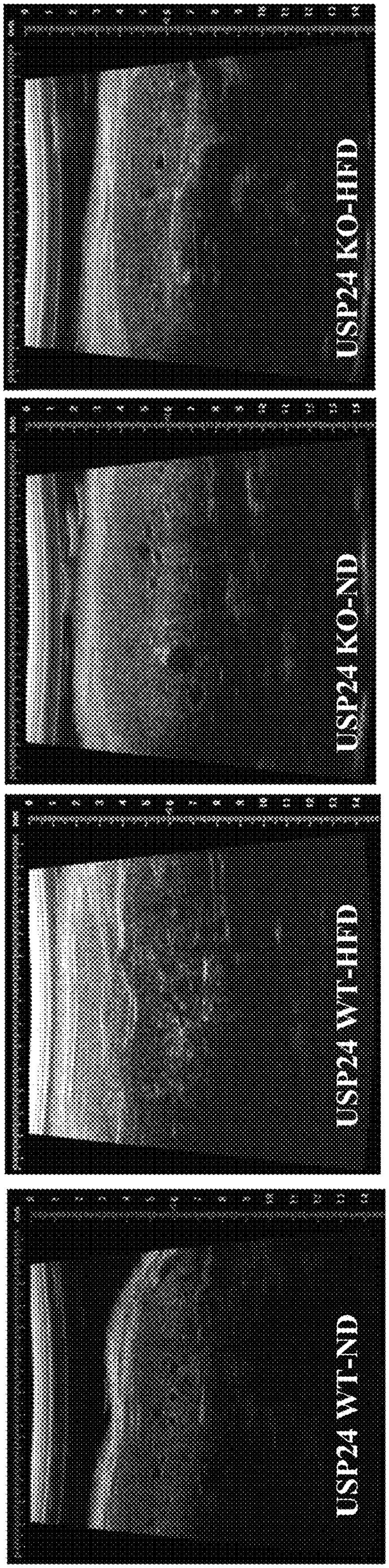

As shown in the results in FIGS. 4A and 4B, after 2 months of a normal diet (ND), neither USP24-WT mice nor USP24-KO mice showed the formation of lipid droplets in their livers (as shown in the top left images of FIG. 4A and the bottom left image of FIG. 4A). After 2 months of HFD, USP24-WT HFD mice exhibited a significant accumulation of lipid droplets in their livers (as shown in the top left images of FIG. 4A), while the livers of USP24-KO HFD mice (bottom left image of FIG. 4A), USP24-WT ND mice treated with USP24-i-a (bottom left image of FIG. 4A), and USP24-WT HFD mice treated with USP24-i-a (bottom left image of FIG. 4A) had few to no lipid droplets.

Additionally, the results from liver ultrasonography in FIG. 4B showed lipid signals in the livers of USP24-WT HFD mice (left image in the second row of FIG. 4B), whereas no such signals were observed in the livers of USP24-WT ND, USP24-KO ND, or USP24-KO HFD mice (images on the left in the first, third, and fourth rows of FIG. 4B). These results indicate that the knockout of the USP24 gene or the use of USP24 inhibitor could specifically target USP24 and inhibit lipid accumulation in the liver, potentially preventing conditions such as fatty liver, nonalcoholic steatohepatitis (NASH), and cirrhosis.

It should be noted that in other embodiments, after evaluating analogs of USP24 inhibitor, USP24-i-a (also known as USP24-i-101, NCI677-08, Formula I-3-1) demonstrated superior inhibition of USP24 activity in comparison to USP24-i1 (Formula I-3-3) (not shown in the figures).

2.4 USP24 Inhibitor Prevented Hepatic Lipid Accumulation

In this embodiment, the analysis of hepatic lipid accumulation and distribution were performed using the Oil-Red-O staining assay. Please referred to FIGS. 5A and 5B, which respectively showed the results of Oil-Red-O staining of liver tissue sections (FIG. 5A) and the percentage (%) of stained areas in accordance with an embodiment of the present invention in USP24 wild-type male (top row in FIG. 5A) or female (bottom row in FIG. 5A) mice after 2 months of a normal diet (ND) or high-fat diet (HFD), followed by the administration of USP24 inhibitor. The USP24 inhibitor was administered by intraperitoneal injection (i.p.) at a dose of 10 mg/kg once a week for two consecutive months. Statistical analysis was conducted using a t-test, where * indicates $p<0.01$, and  indicates $p<0.005$ (FIG. 5**B).

Figure 5A:
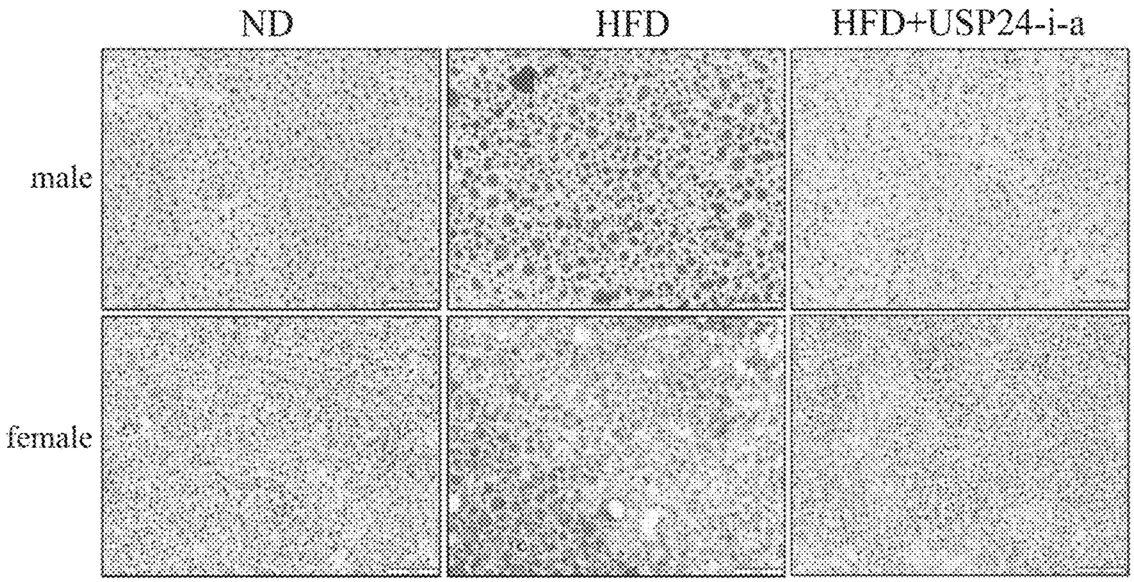
FIG. 5A and FIG. 5B respectively show liver tissue sections stained with Oil-Red-O (FIG. 5A) and scatter plot of the percentage of stained areas (%) in male (as shown in upper row in FIG. 5A) or female (s shown in lower row in FIG. 5A) USP24 wild-type mice in one embodiment of the present invention after 2 months of normal diet (ND) or high-fat diet (HFD) followed by administration of a USP24 inhibitor.
Figure 5B:
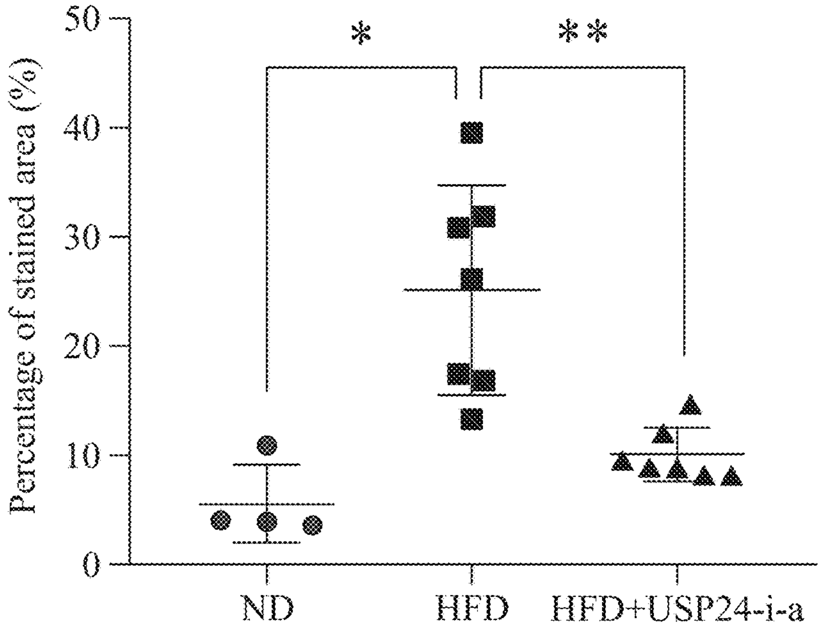

The results in FIGS. 5A and 5B showed that in the livers of USP24-WT ND mice, only faint signals of Oil-Red-O staining were observed, whereas the accumulation of lipid content in the livers of USP24-WT HFD mice significantly increased. Following the administration of USP24-i-a to USP24-WT HFD mice, the signals of Oil-Red-O staining in the liver were significantly reduced or nearly disappeared, indicating that USP24 inhibitor could markedly inhibit hepatic lipid accumulation.

2.5 USP24 Inhibitor Reduced Lipid Droplets, PPAR-γ, and PLIN1 in Adipocytes

Previous studies had indicated that the formation of adipocytes was a major cause to weight gain and lipid accumulation. In this embodiment, an in vitro cellular model was utilized to assess the impact of USP24 inhibitor on the differentiation of cells into adipocytes.

Figure 6A:
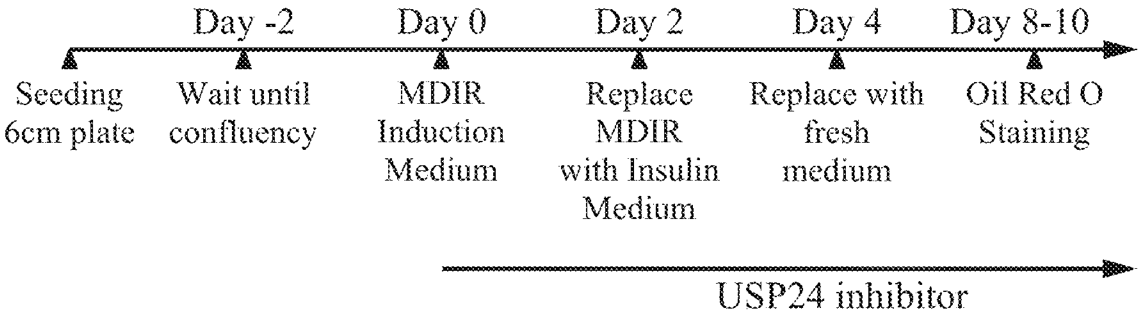
FIG. 6A shows the experimental flowchart for evaluating the differentiation of 3T3-L1 cells into adipocytes with USP24 inhibitor treatment according to one embodiment of the present invention.

Please referred to FIG. 6A, which illustrated the experimental procedure for evaluating the effects of USP24 inhibitor on the induction of 3T3-L1 cells into adipocytes according to an embodiment of the present invention. When 3T3-L1 cells reached approximately 70% confluence, the MDIR induction medium containing USP24 inhibitor (5 μM or 10 μM) was added to the cells on day 0 and cultured for 2 days. Subsequently, on day 2, the induction medium was replaced with fresh medium containing USP24 inhibitor (5 μM or 10 μM) and insulin (10 μg/mL), and the cells were cultured for an additional 2 days. Next, the culture medium was changed the fresh medium containing USP24 inhibitor on day 4, and the cells were cultured for 4-6 more days, allowing 3T3-L1 cells to differentiate into adipocytes or adipocyte-like cells. And then, the cells were stained with Oil-Red-O (on days 8-10) to assess the influence of USP24 inhibitor on adipocyte formation, as shown in FIGS. 6B and 6C.

The MDIR induction medium included 0.5 mM 3-isobutyl-1-methylxanthine (IBMX), 1 μM dexamethasone (D), 1.5 g/mL insulin (I), and 1 μM rosiglitazone (R) in Dulbecco's Modified Eagle Medium (DMEM). The components M, D, R, and USP24 inhibitor were dissolved in dimethyl sulfoxide (DMSO) and then added to DMEM. The insulin culture medium contained 10 μg/mL insulin in DMEM, and the fresh medium included 10% fetal bovine serum (FBS) in DMEM.

Figure 6B:
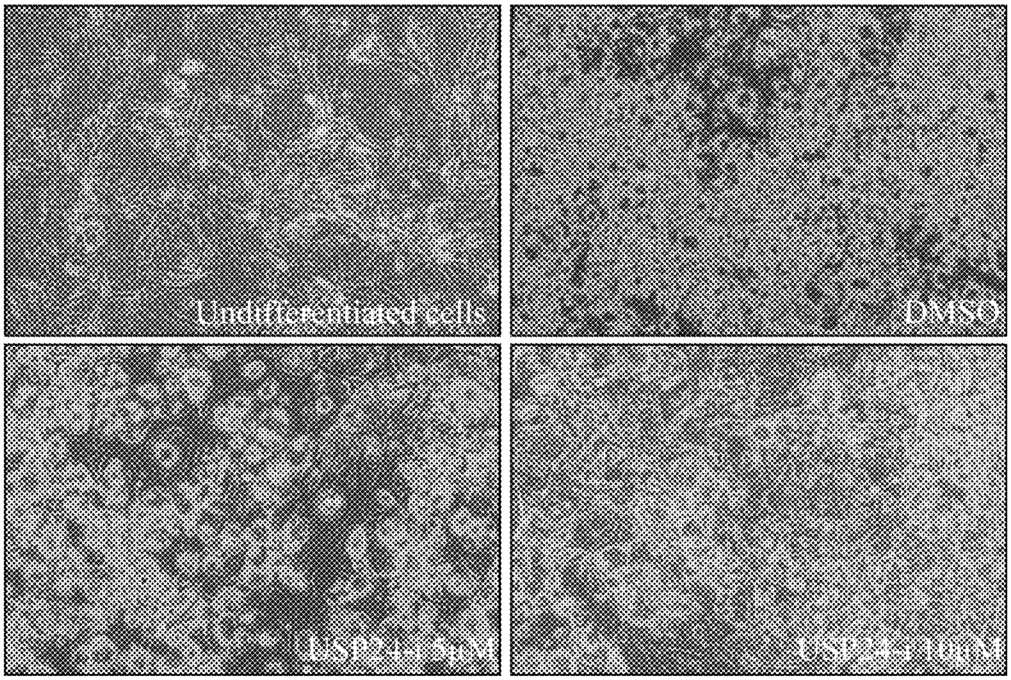
FIG. 6B and FIG. 6C show images of the gross appearance (FIG. 6B, optical microscope, 100× magnification) and Oil-Red-O staining (FIG. 6C, optical microscope, 100× magnification) of 3T3-L1 cells treated with a USP24 inhibitor in one embodiment of the present invention.
Figure 6C:
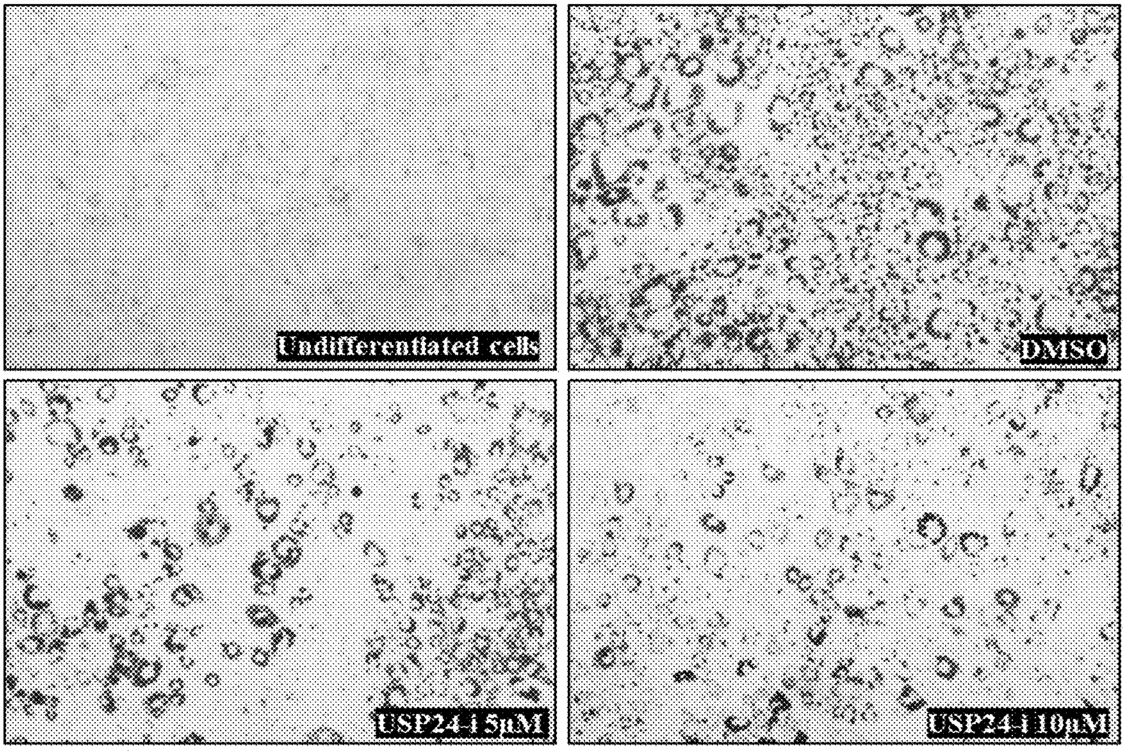

Please referred to FIGS. 6B and 6C, which respectively showed images of 3T3-L1 cells according to an embodiment of the present invention in terms of gross appearance (FIG. 6B, optical microscope, 100× magnification) and Oil-Red-O staining (FIG. 6C, optical microscope, 100× magnification). The results in FIGS. 6B and 6C indicated that in comparison to undifferentiated cells (top-left images in FIGS. 6B and 6C), differentiated cells treated with DMSO exhibited a significant accumulation of lipid droplets, successfully inducing adipocyte formation, as shown in the top-right images in FIGS. 6B and 6C. However, 3T3-L1 cells treated with USP24-i-a exhibited a significant reversal of lipid droplet accumulation, and this effect was dose-dependent, as demonstrated in the bottom-left (5 μM USP24-i-a treatment) and bottom-right (10 μM USP24-i-a treatment) images in FIGS. 6B and 6C. It suggested that treatment with USP24-i-a could inhibit adipocyte formation, thereby reducing body weight and lipid accumulation in the liver.

It was known that PPAR-γ and PLIN1 were important markers for adipocytes. In this embodiment, commercially available antibodies were used to perform Western blotting on 3T3-L1 cells to evaluate the expression levels of proteins associated with adipocyte formation in response to USP24-i-a treatment, as shown in FIGS. 7A to 7G.

Figure 7A:
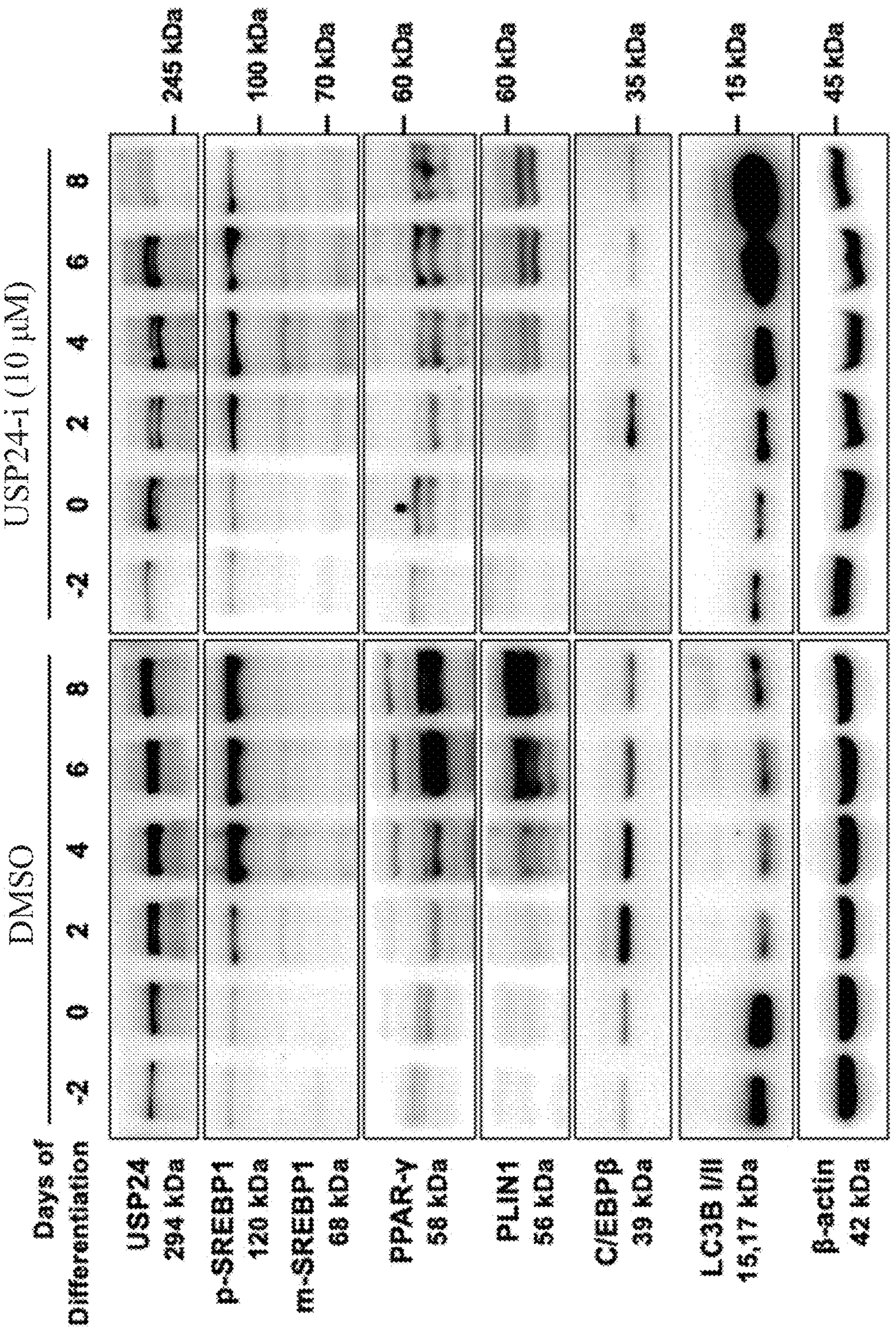
FIGS. 7A to 7G shows the Western blot analysis results (FIG. 7A) and curve graphs (FIGS. 7B to 7G) of adipogenesis gene expression levels of 3T3-L1 cells treated with a USP24 inhibitor according to one embodiment of the present invention.

Please referred to FIG. 7A, which showed the results of Western blot analysis of 3T3-L1 cells treated with USP24 inhibitor according to an embodiment of the present invention. The results in FIG. 7A demonstrated that in comparison to 3T3-L1 cells treated with DMSO (labeled with the circle symbol), differentiated 3T3-L1 cells treated with USP24-i-a (labeled with the square symbol) exhibited reduced adipogenesis expression levels of PPAR-γ and PLIN1 (Perilipin 1), and this effect was dose-dependent, as shown in FIGS.

Figure 7B:
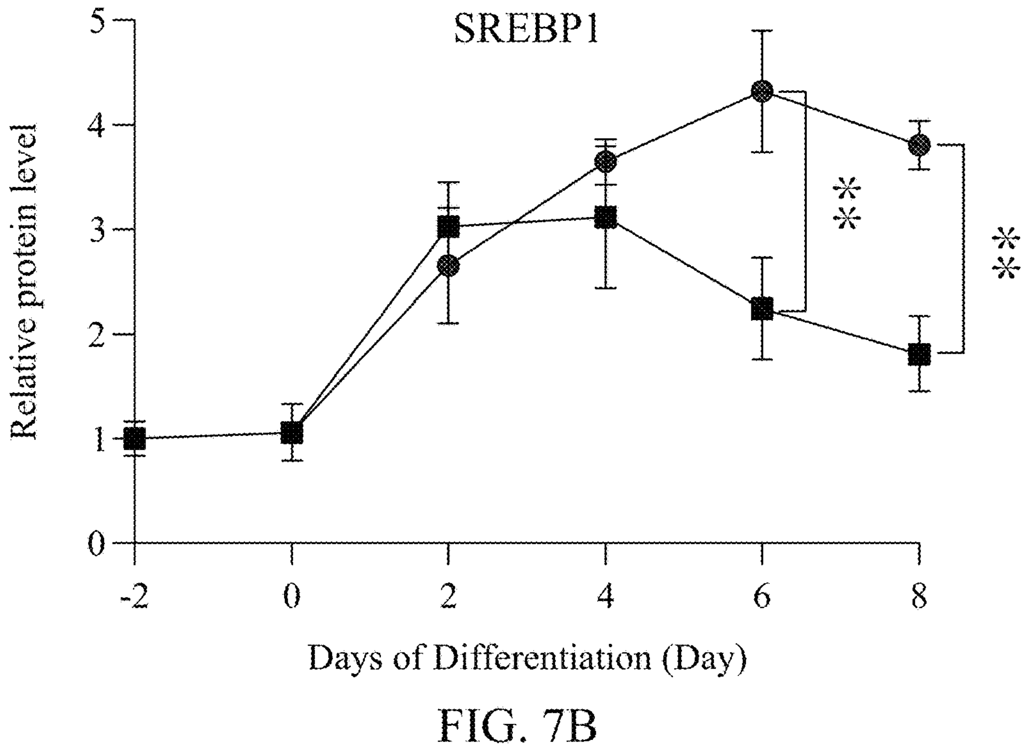
Figure 7C:
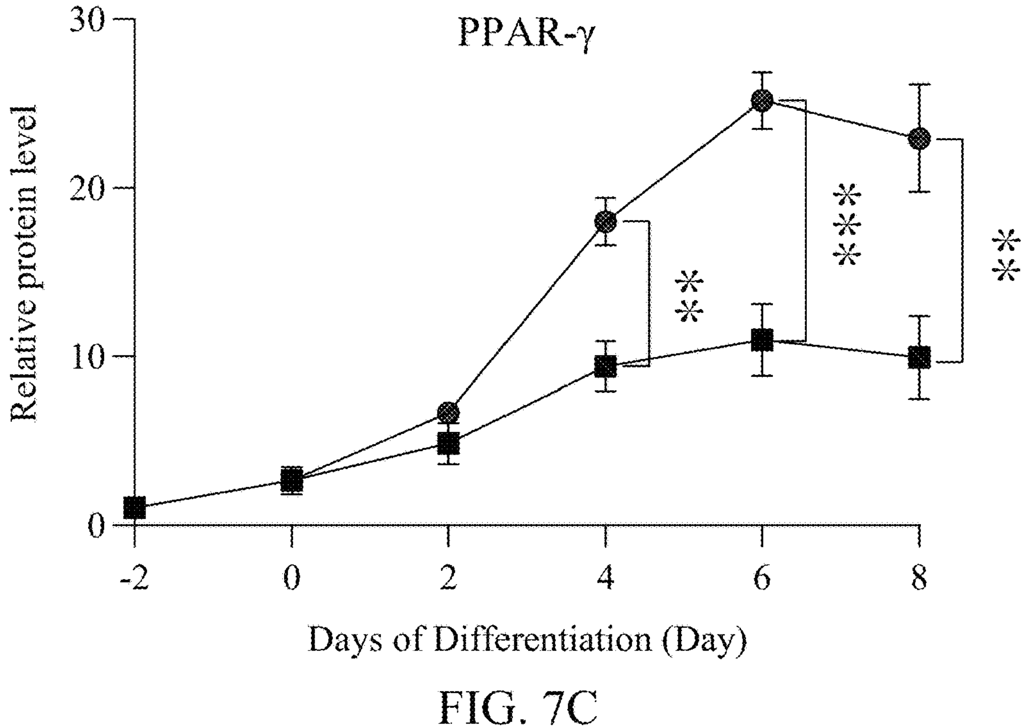
Figure 7D:
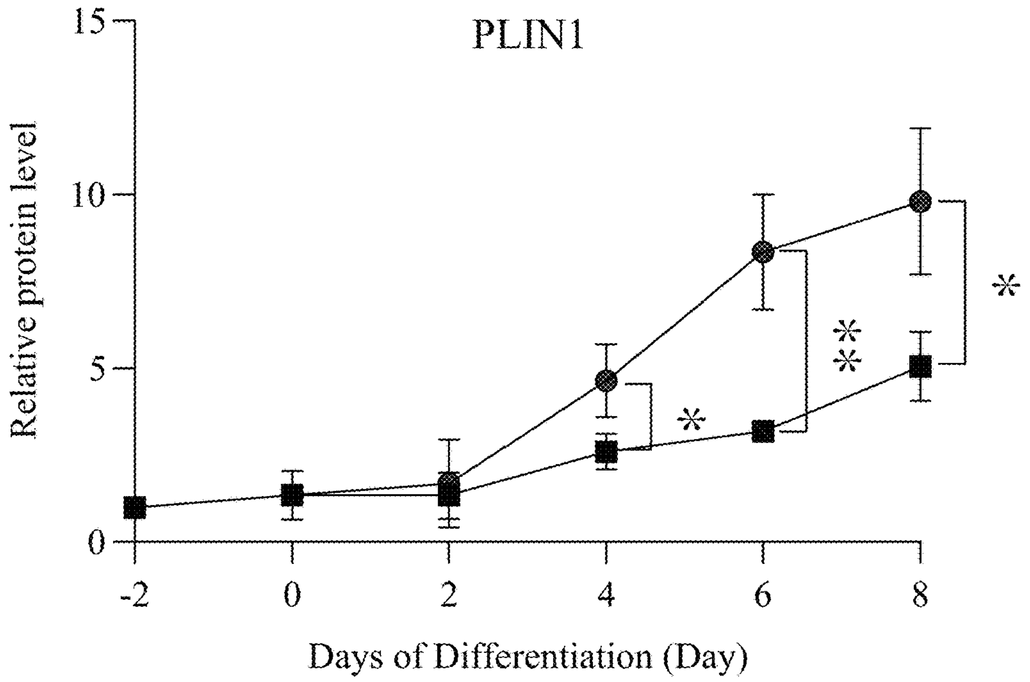
Figure 7E:
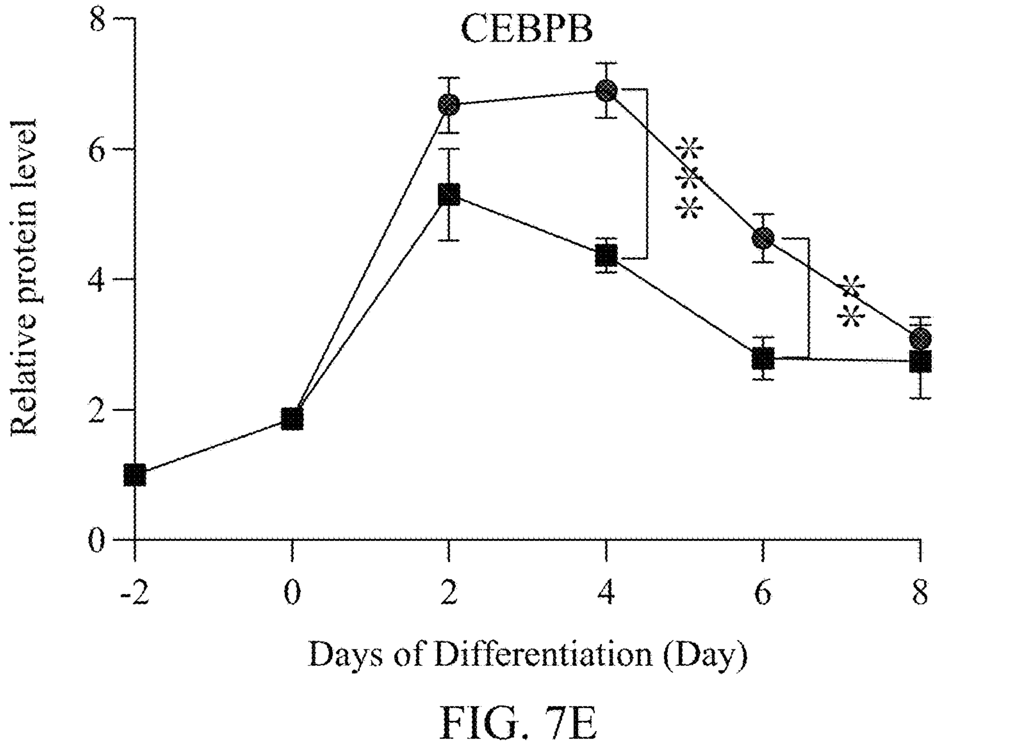
Figure 7F:
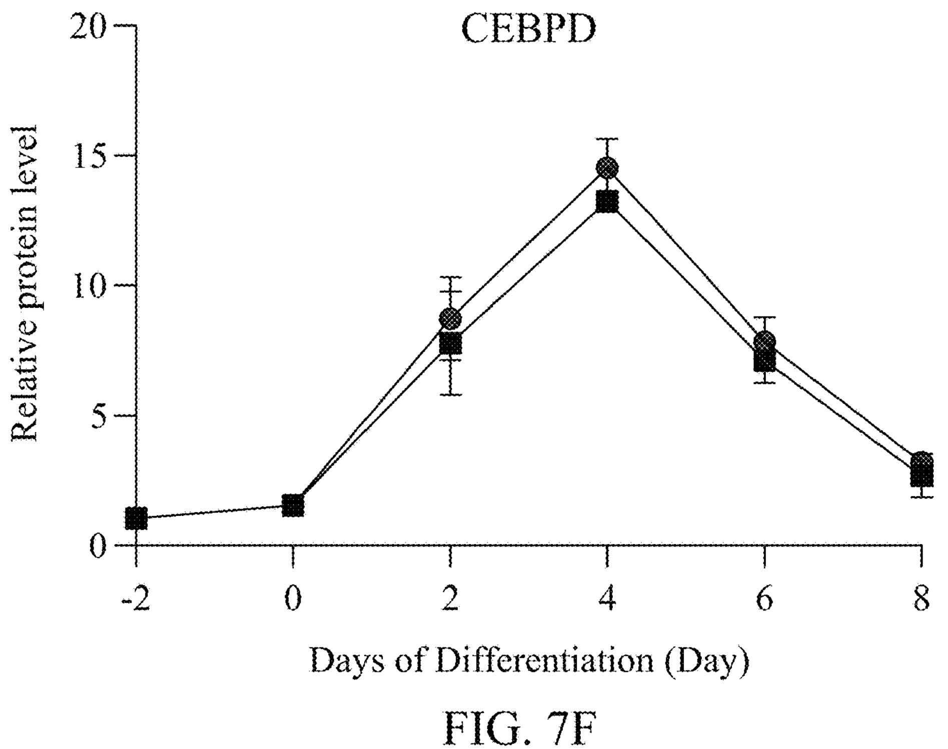
Figure 7G:
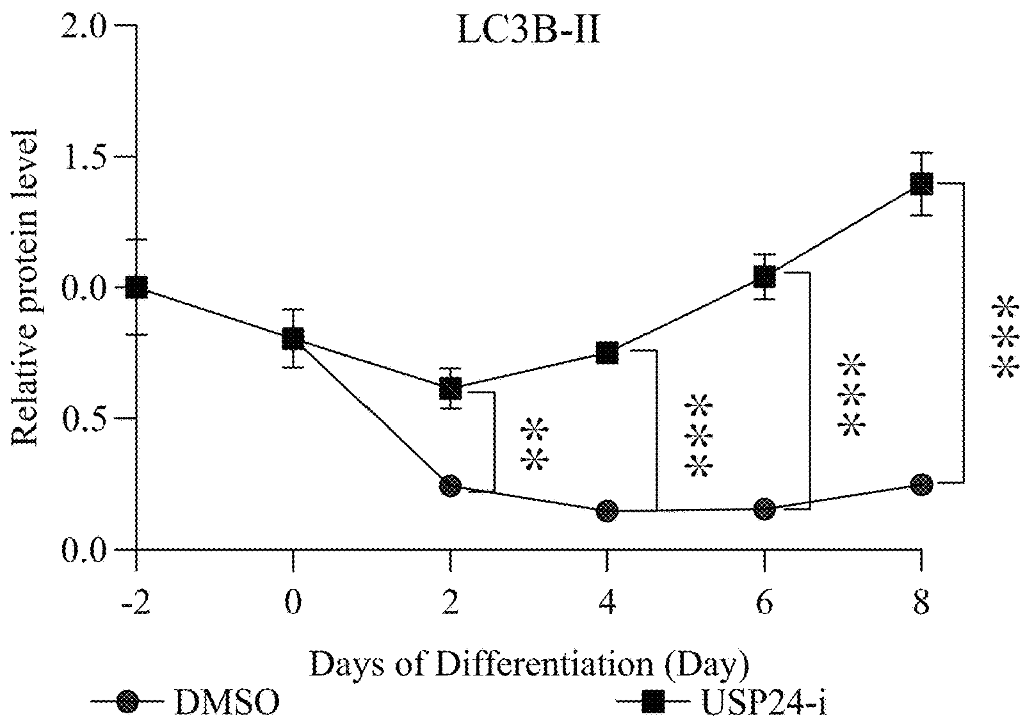
Figure 8A:
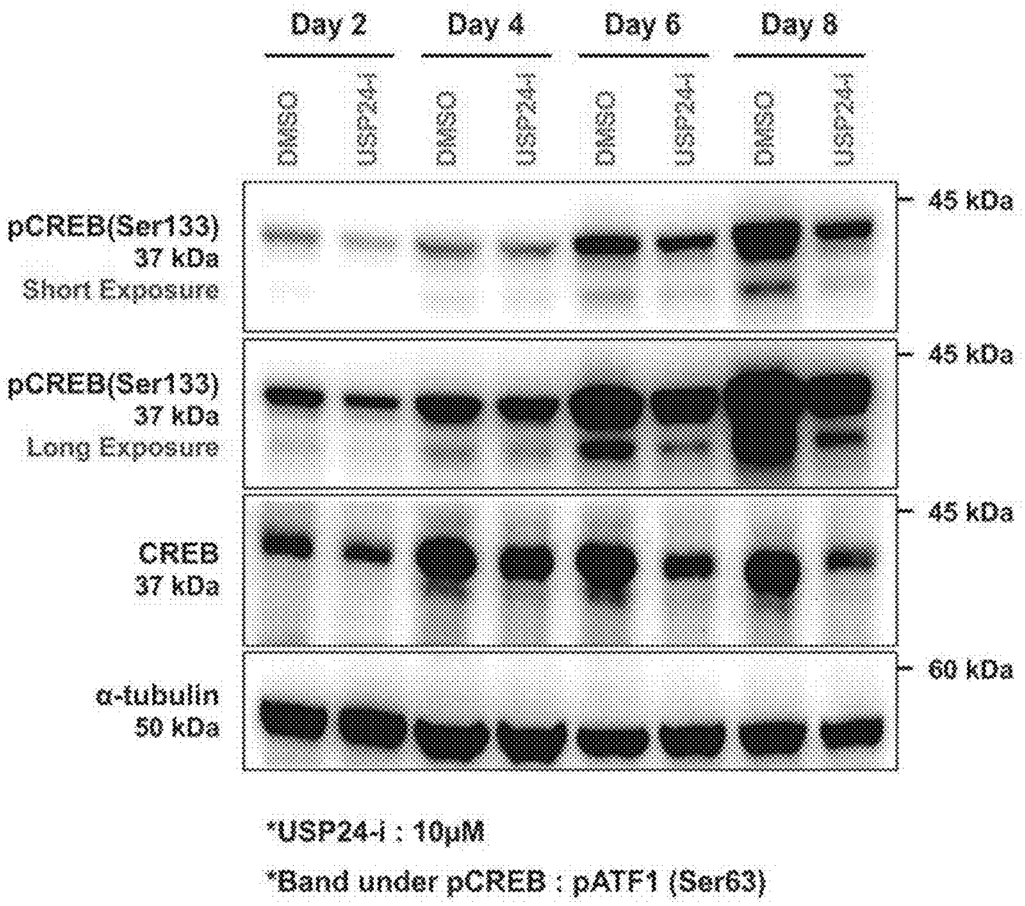
FIG. 8A to FIG. 8D respectively show the serological test results of USP24 wild-type mice in one embodiment of the present invention after 2 months of normal diet (ND) or high-fat diet (HFD).
Figure 8B:
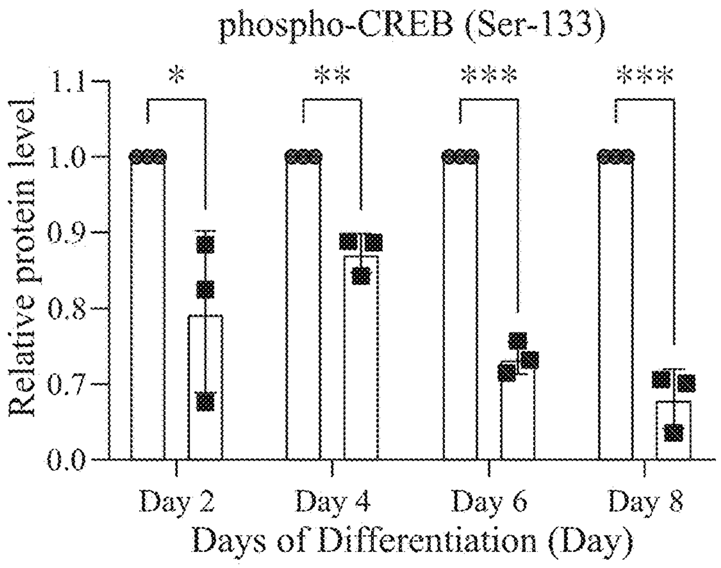
Figure 8C:
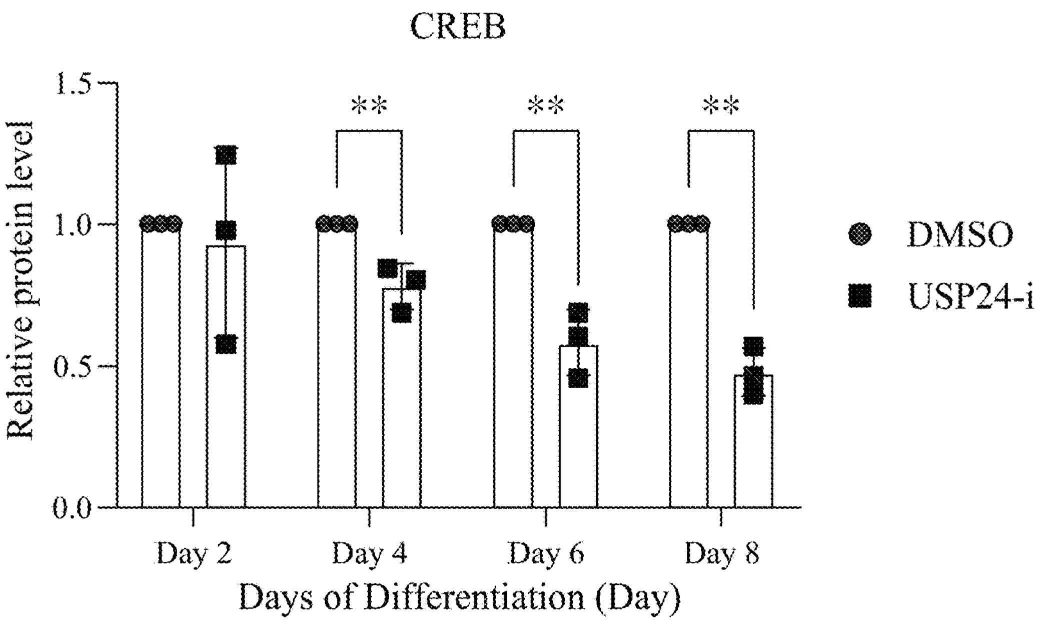
Figure 8D:
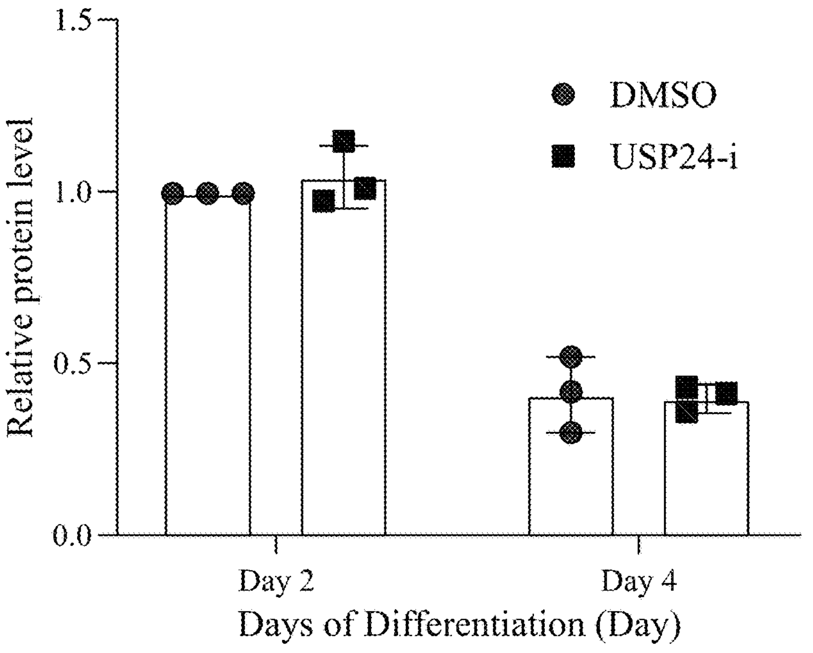

7C and 7D. Additionally, the adipogenesis expression levels of other proteins such as SREBP1 and C/EBPβ were also reduced, as shown in FIGS. 7B, 7E and 7F. This indicated that USP24-i-a treatment could decrease the levels of PPAR-γ and PLIN1 in differentiated 3T3-L1 cells, thereby inhibiting the formation of adipocytes.

As shown in FIGS. 8A to 8D, USP24-i-101 inhibited CREB and its phosphorylation, indicating that CREB as a driver for 3T3-L1 differentiation.

Figure 9A:
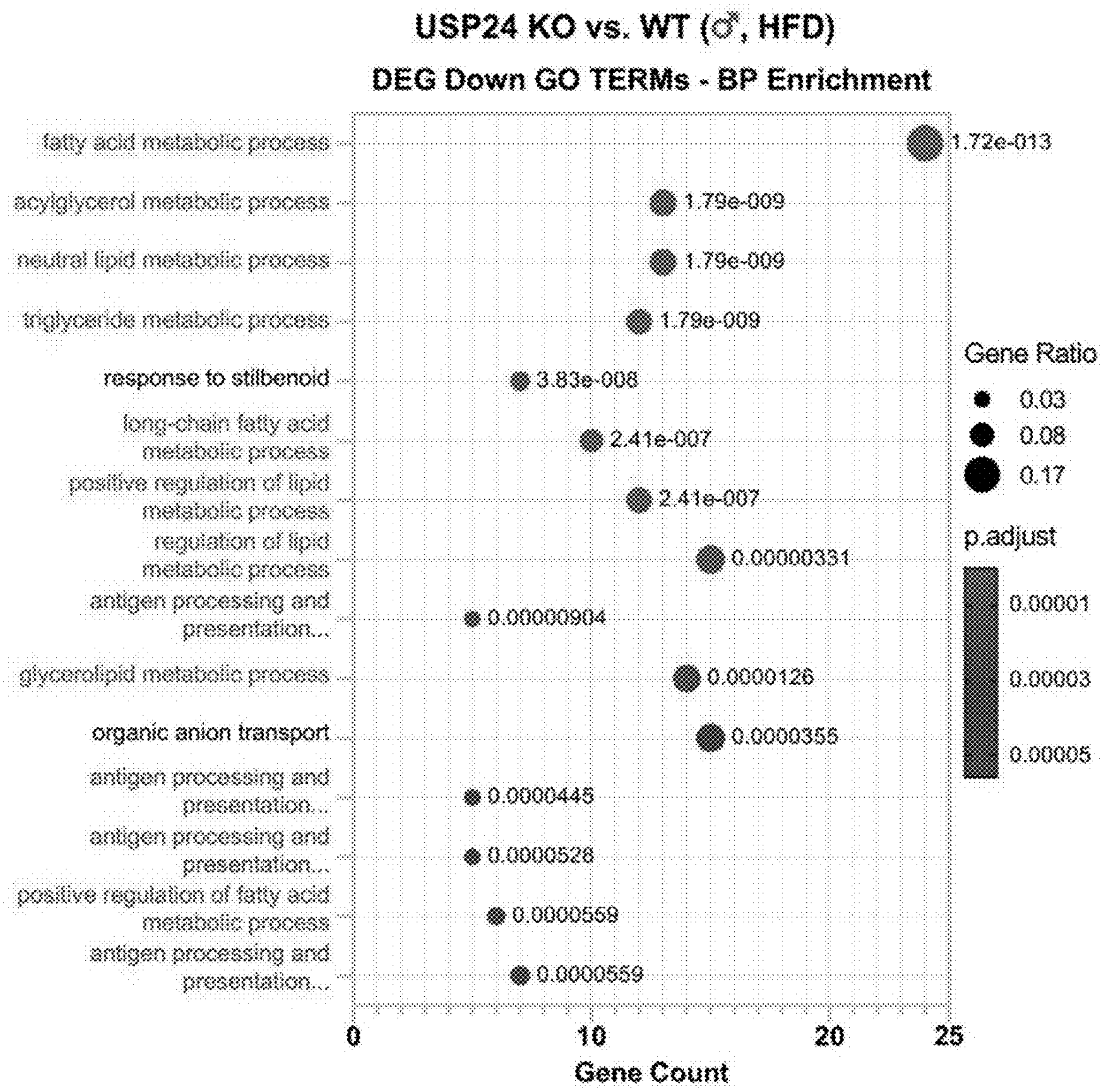
FIGS. 9A and 9B respectively show the global gene expression profiles by RNA-seq in one embodiment of the present invention.
Figure 9B:
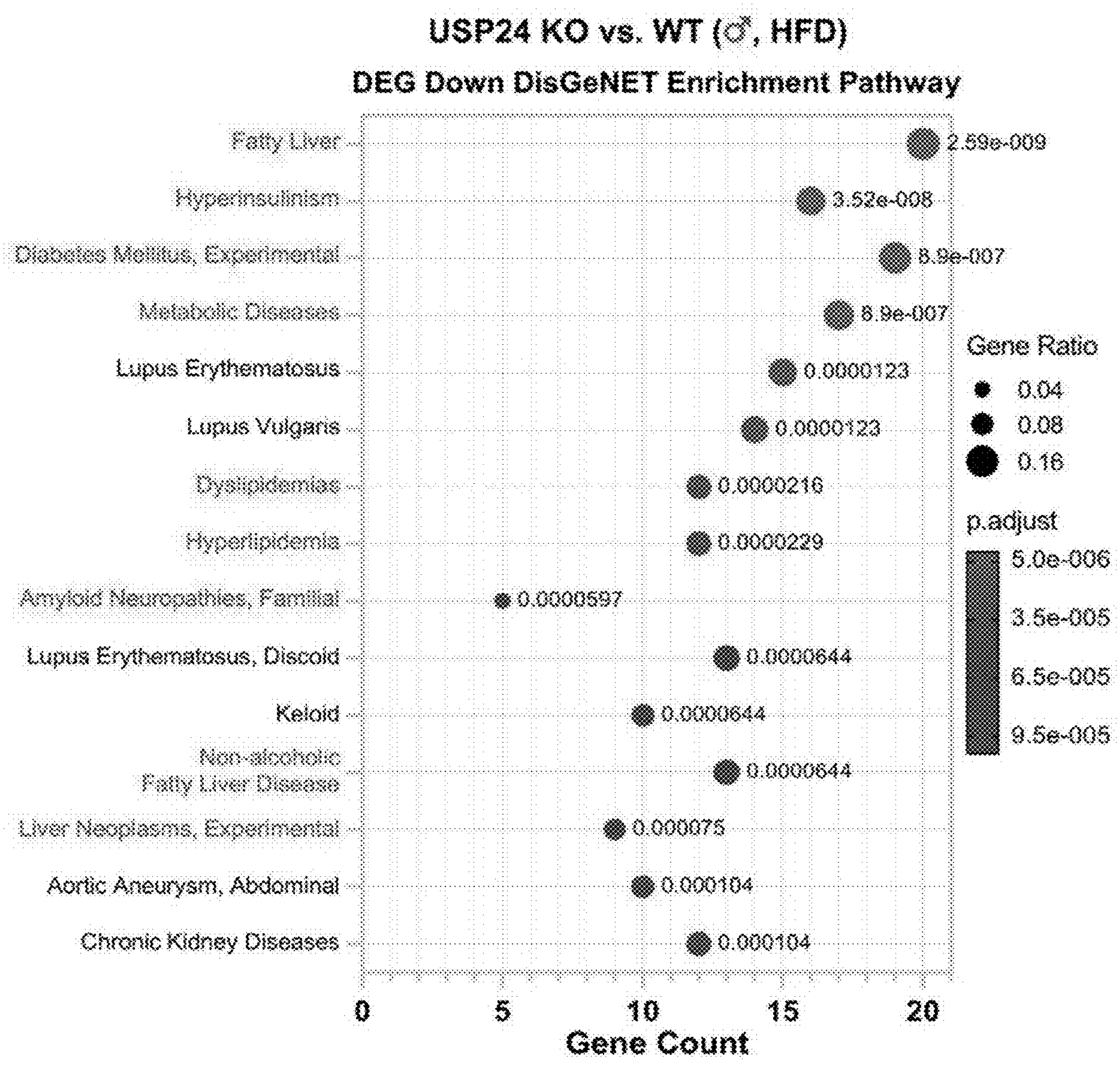

As shown in FIGS. 9A and 9B, RNA samples were isolated from liver tissues of USP24WT and USP24KO mice for studying the global gene expression profiles by RNA-seq. Data indicated that several lipogenesis related pathways were down regulated under knockout of USP24.

2.6 USP24-i-101 Safety Assay

As shown in FIGS. 10A to 10H, serum were collected from normal diet (ND) and high fat diet (HFD) mice with or without USP24-i-101 treatment to study the safety assay by ELISA assay. In the USP24-i-101 treated HFD-mice, the GPT, GOT and total cholesterol were significantly inhibited, but the total protein (TP), albumin (ALB) and triglyceride (TG) did not significantly change.

2.7 USP24 Inhibitor Could Improve Liver Activity

In this Example, wild-type mice were fed a normal diet (ND) or a high-fat diet (HFD), and they were injected intraperitoneally (i.p.) with 10 mg/kg of USP24-i once a week for two consecutive months. Subsequently, mouse sera were collected, and serum-related indices were examined to assess the impact of USP24-i on lipogenesis and liver function, as depicted in FIGS. 10A to 10H.

Figure 10A:
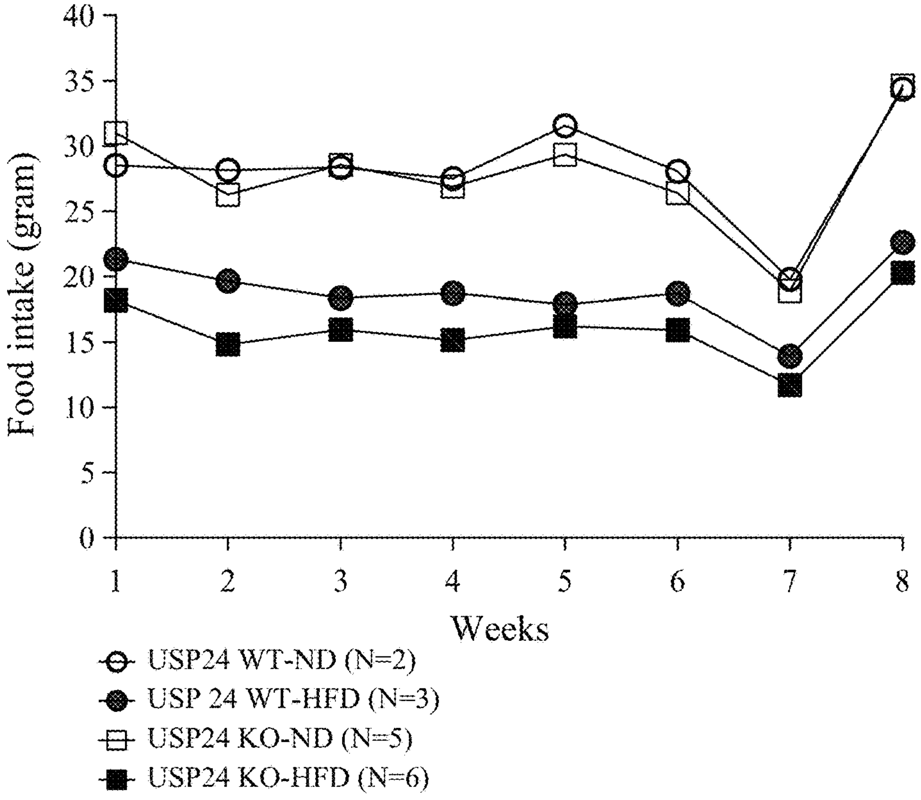
FIGS. 10A to 10H show the results of serum tests according to an embodiment of the present invention for wild-type mice after 2 months of normal diet (ND) or high-fat diet (HFD) feeding.
Figure 10B:
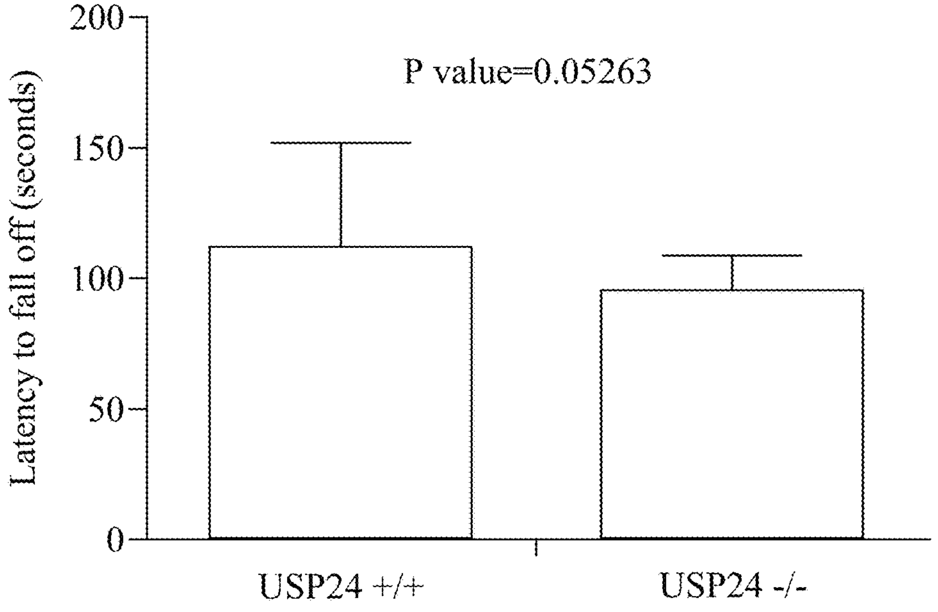
Figure 10C:
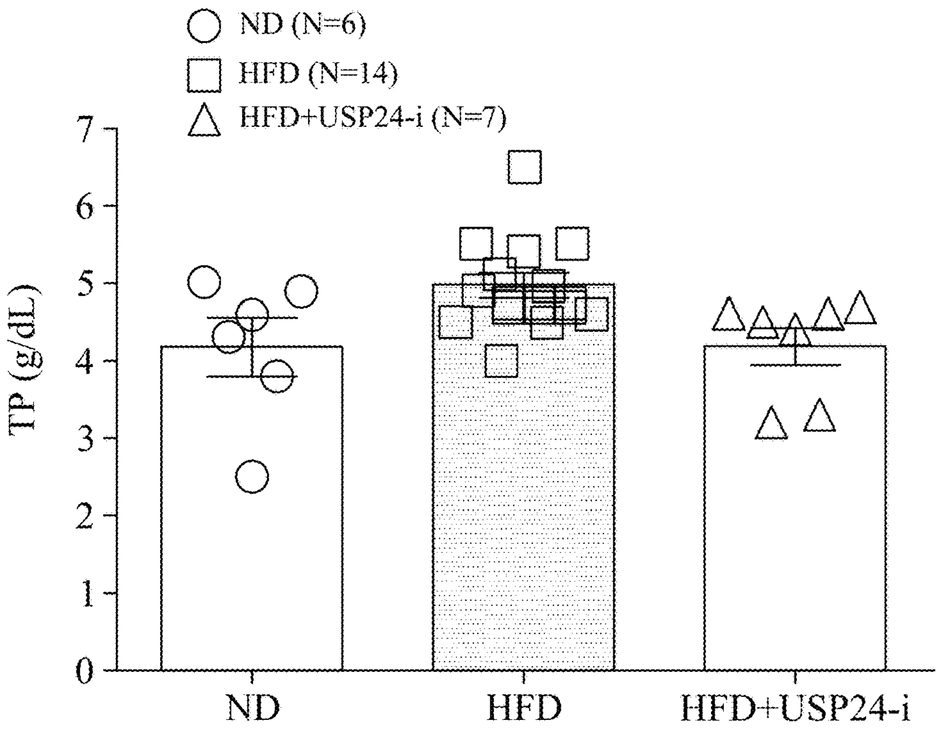
Figure 10D:
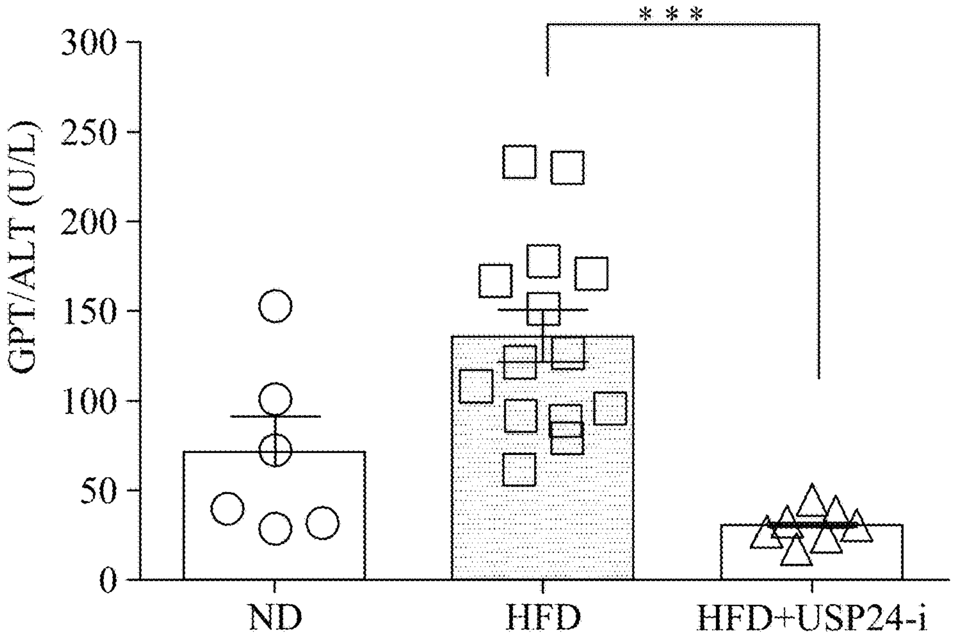
Figure 10E:
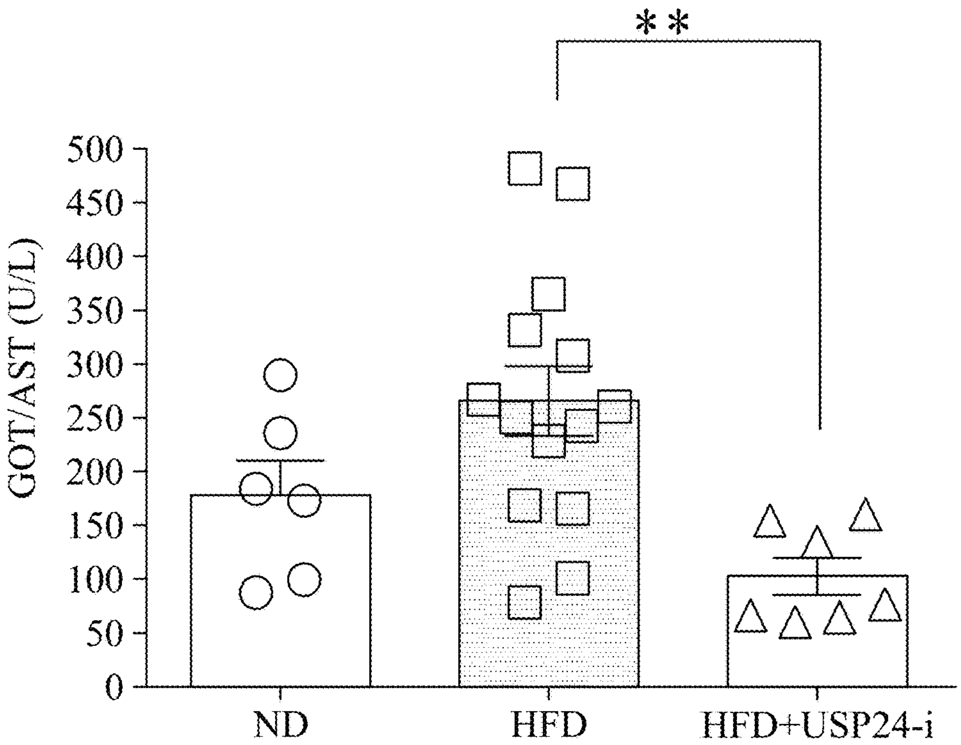
Figure 10F:
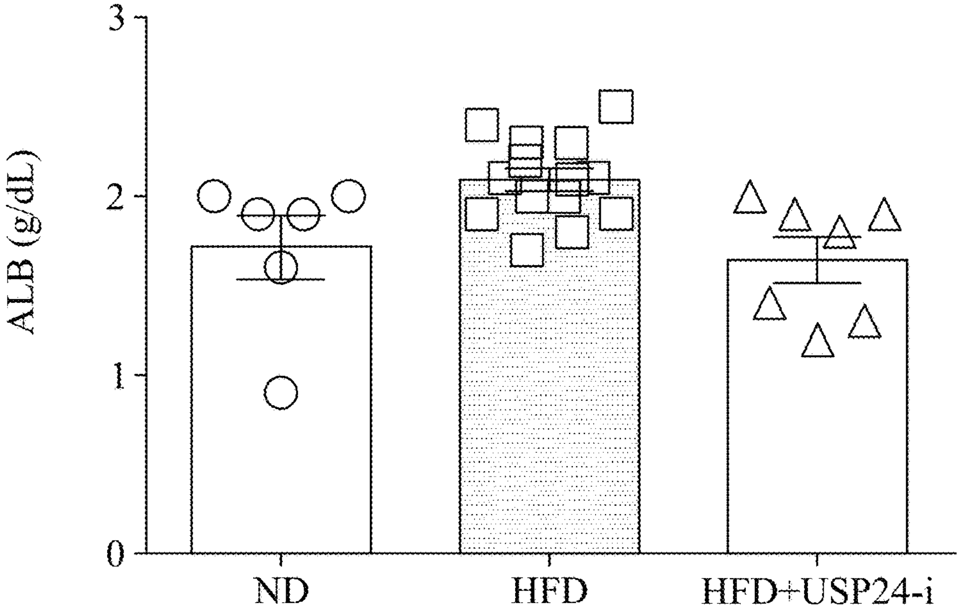
Figure 10G:
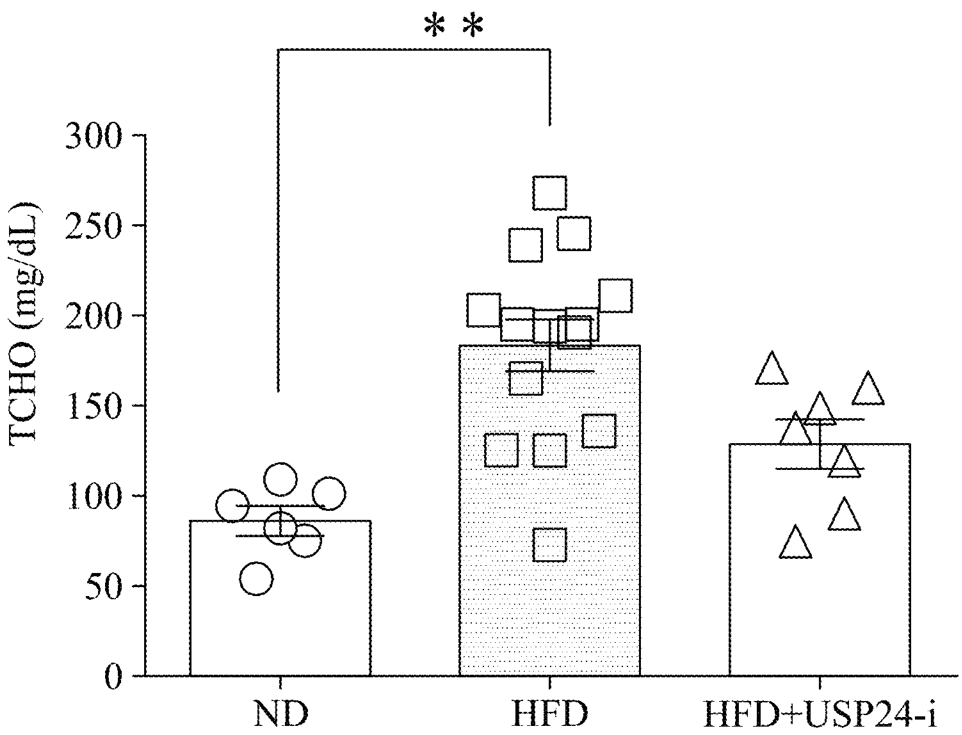
Figure 10H:
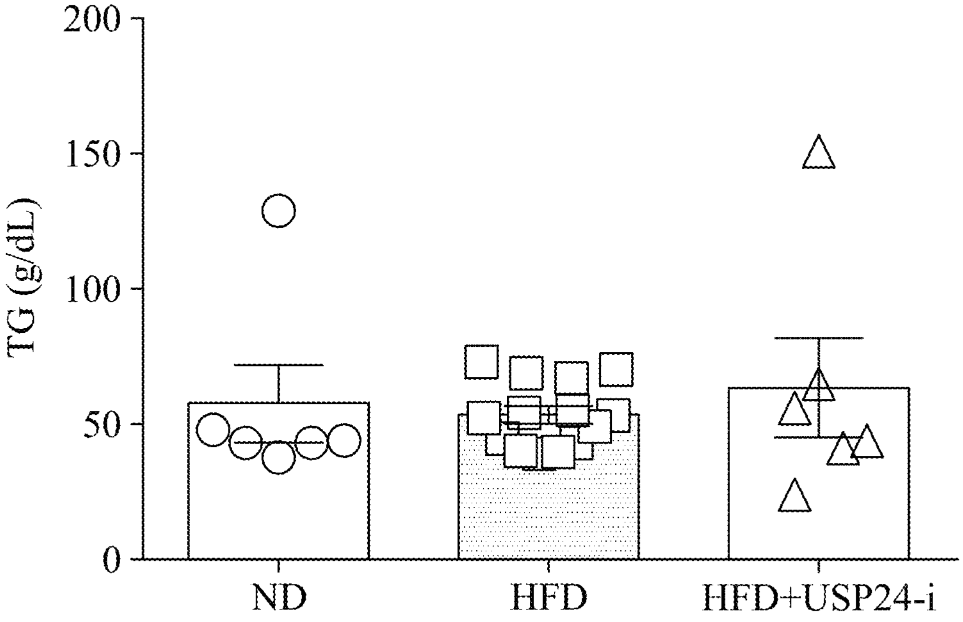

Please referred to FIGS. 10A to 10H, which showed the results of serum tests according to an embodiment of the present invention for wild-type mice after 2 months of normal diet (ND) or high-fat diet (HFD) feeding. The mice of all groups had stably food intake on weeks 1 to 6, as shown in FIG. 10A. There was no statistically significant difference of the time of latency to fall off the rotarod between the USP 24 KO mice and the wild-type USP 24 mice, as shown in FIG. 10B. Mouse sera were collected from normal diet (ND) and high fat diet (HFD) mice with or without USP24-i treatment to perform the safety evaluation by ELISA assay. In the USP24-i treated HFD-mice, the GPT (glutamic pyruvic transaminase), GOT (glutamic oxalo-acetic transaminase) and total cholesterol were significantly inhibited but the total protein (TP), albumin (ALB) and triglyceride (TG) did not significantly change, as shown in FIG. 10C to 10H. Therefore, USP24 inhibitor could inhibit the lipogenesis, thereby improving liver activity.

Figure 11A:
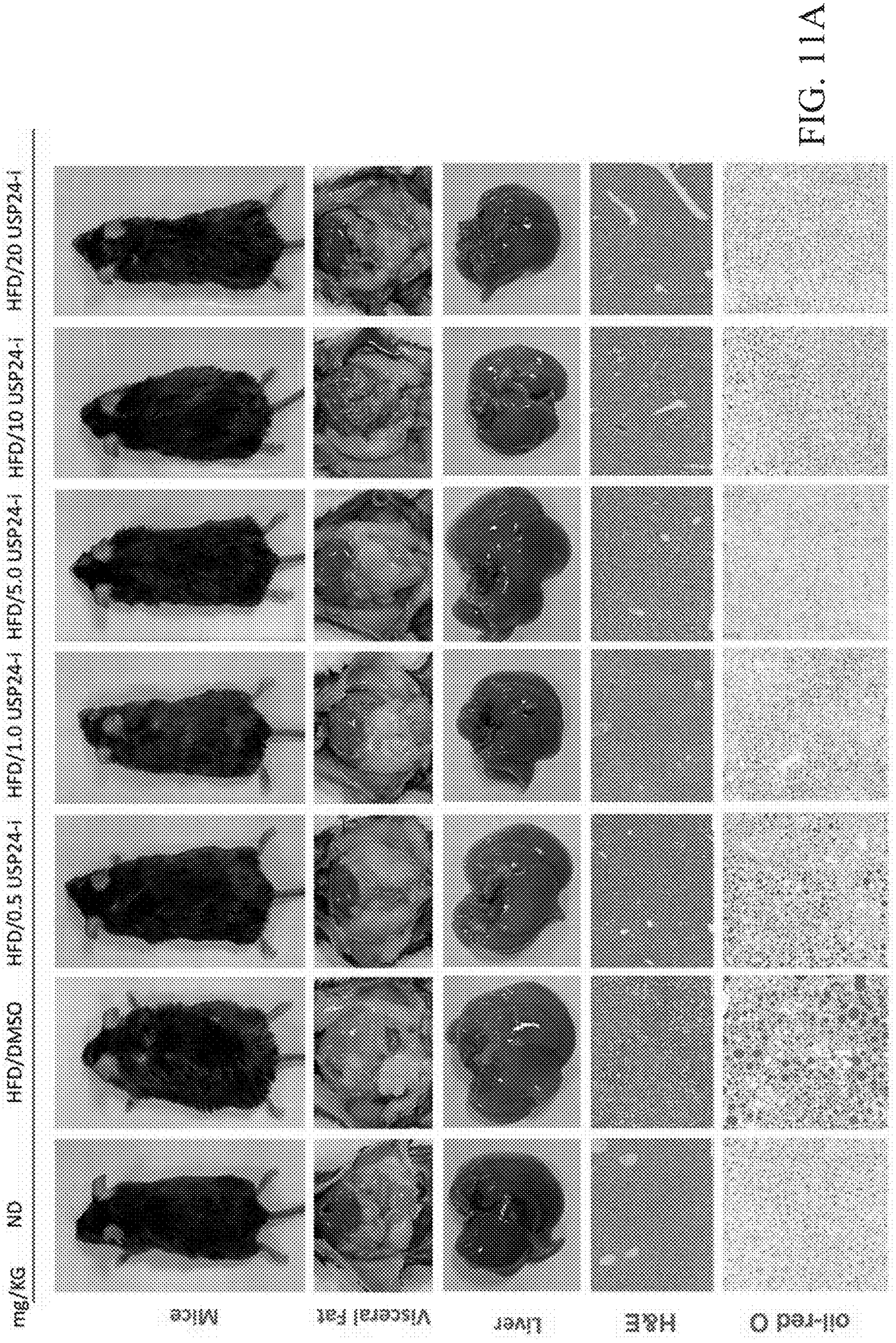
FIGS. 11A to 11C shows the images of the gross appearance and major organs, stained tissue sections of liver, body weight (FIG. 11B) and Oil-Red-O-stained area percentage (FIG. 11C) of liver tissues of USP24 knockout (KO) mice after fed with high-fat diet (HFD) or normal diet (ND) followed by the treatment of USP24-i according to one embodiment of the present invention.
Figure 11B:
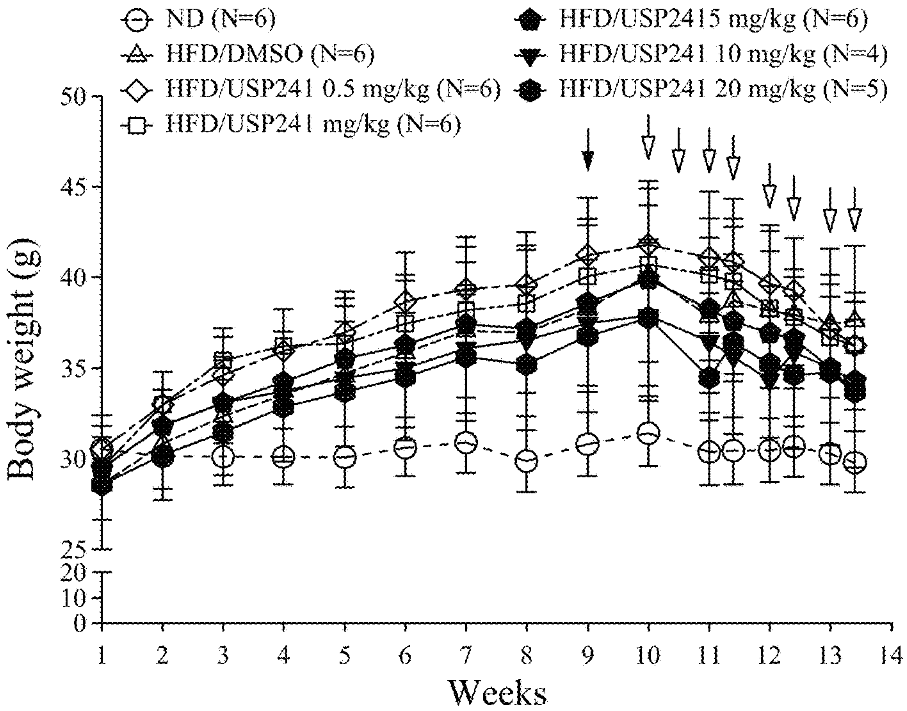
Figure 11C:
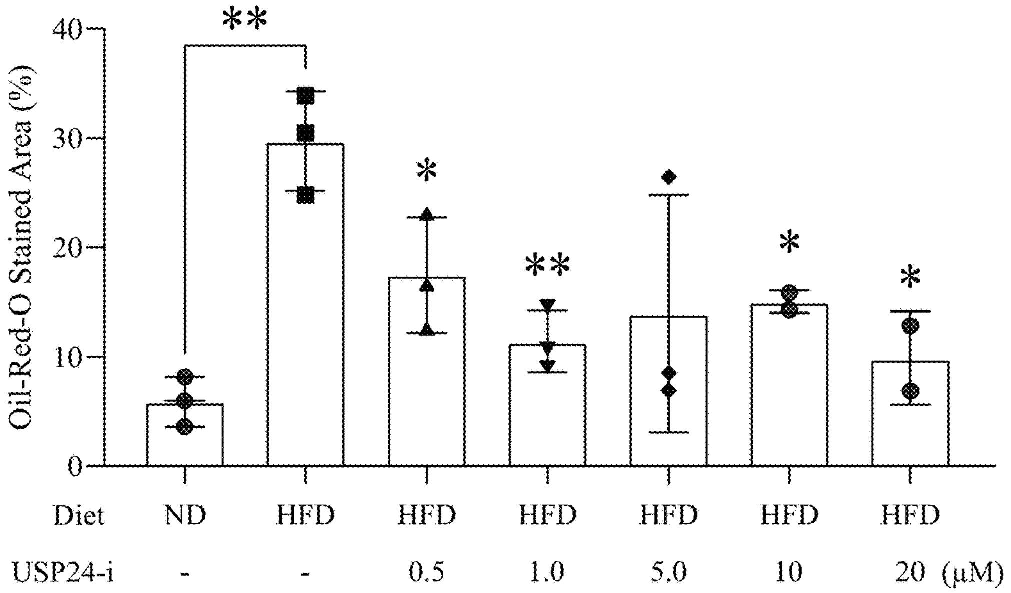

In the previous studies of the inventors, USP24-i-101 treated (i.p.) the HFD mice from the initiation of the experiment. Those results revealed that the body weight and fatty liver could be inhibited. In this Example, USP24-i-101 treated the mice after obesity, not from initiation. Mice were fed with HFD for two months and then treated with USP24-i-101 one month (two times per week, i.p.). As shown in FIG. 11A, the visceral fat and fatty liver (FIG. 11A and FIG. 11C) were really decreased after USP24-i-101 treatment. In addition, the body weight was significantly decreased under USP24-i-101 treatment (FIG. 11B).

Figure 11D:
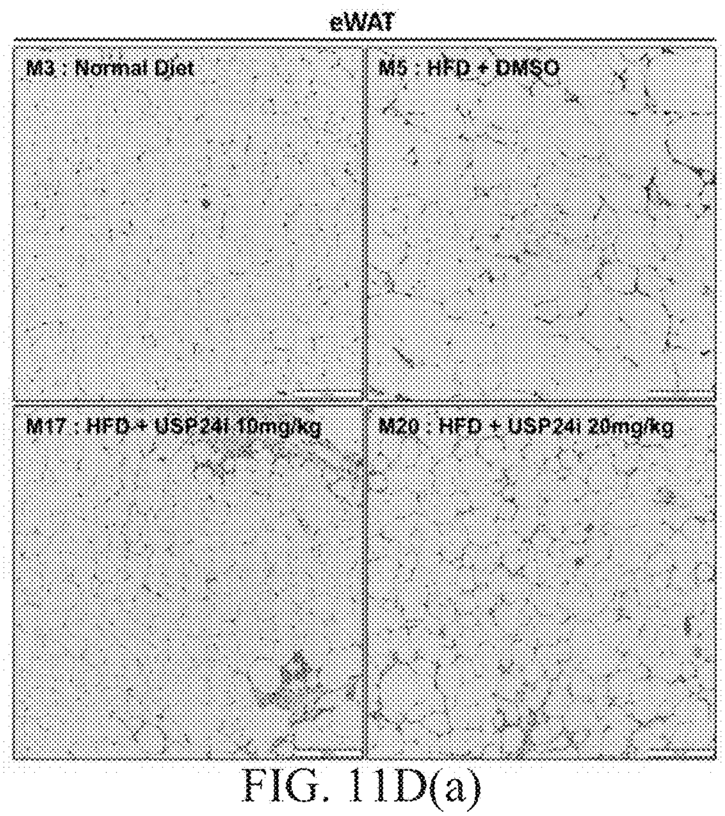
FIGS. 11D(a) to 11D(d) show the images of eWAT and iWAT of mice inhibited by USP24-i-101 according to one embodiment of the present invention.
Figure 11D:
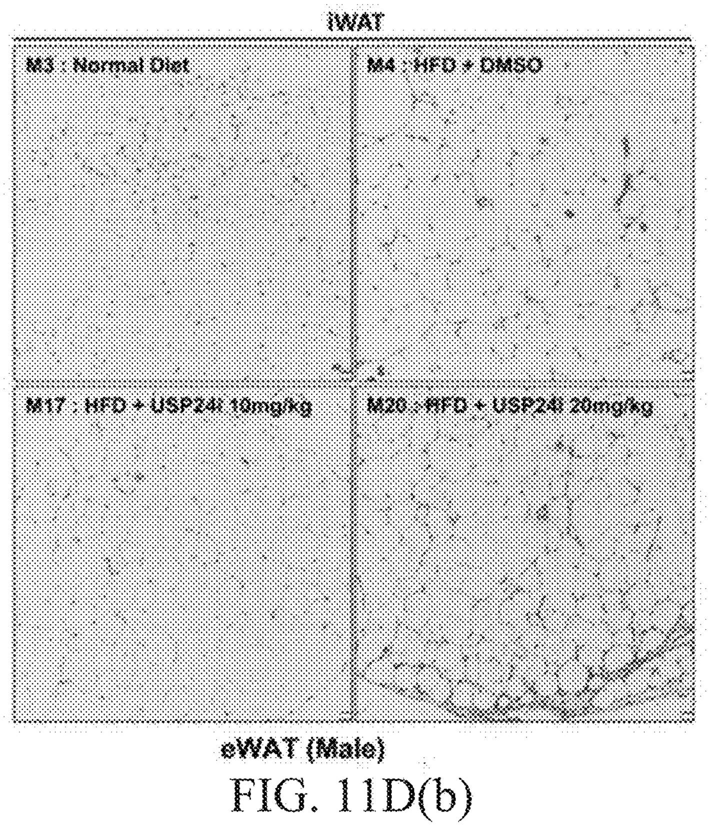
Figure 11D:
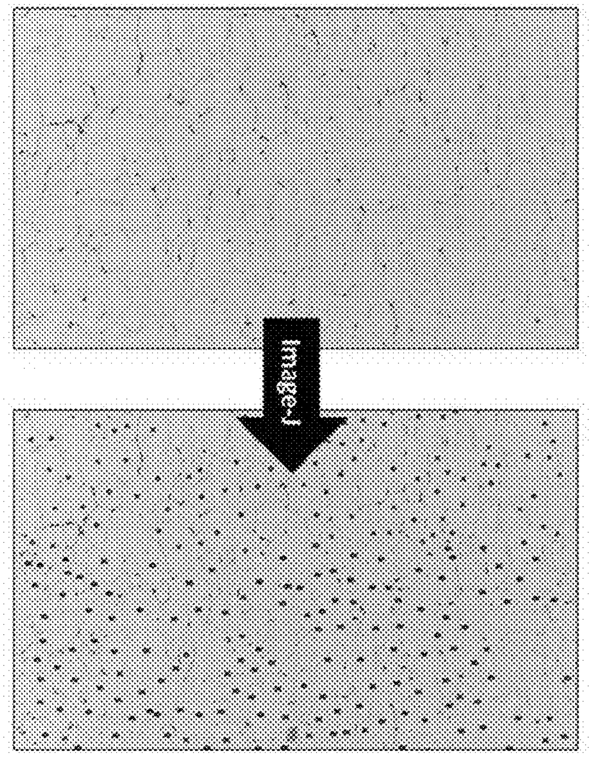
Figure 11D:
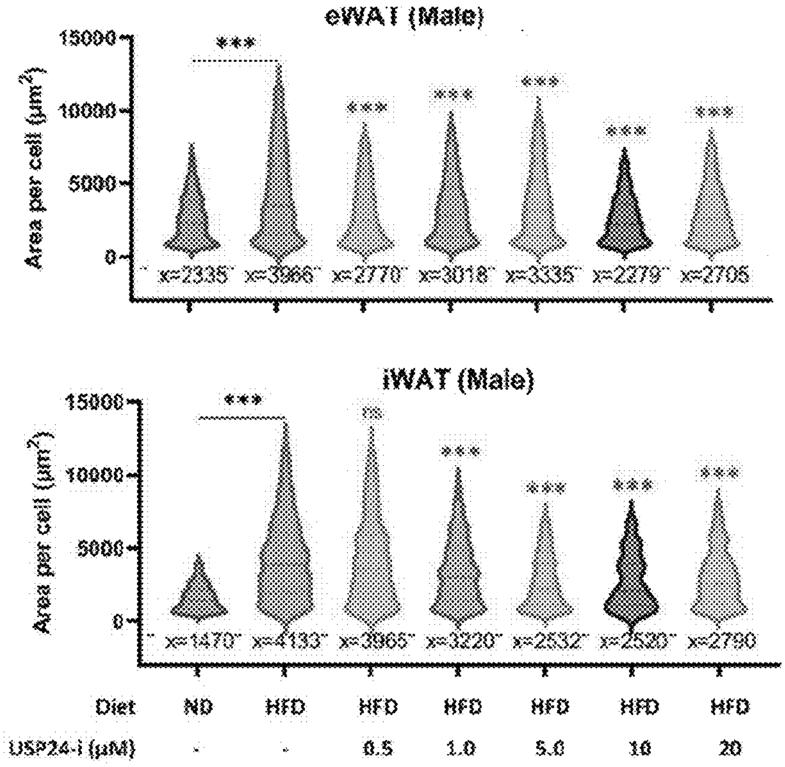

In addition, USP24-i-101 could inhibit eWAT and iWAT of mice. The subcutaneous fat and visceral fat (around organs such as kidney and reproductive organs) were collected to analyze the size of the epididymal WAT [eWAT, as shown in FIG. 11D (a), upper panel of FIG. 11D(c) and upper panel of FIG. 11D(d)] and inguial WAT [iWAT, as shown in FIG. 11D(b), lower panel of FIG. 11D(c) and lower panel of FIG. 11D(d)]. Those results indicated that the size of eWAT and iWAT were increased but could be inhibited under USP24-i-101 treatment. In summary, targeting USP24 not only inhibited fatty liver but also inhibited subcutaneous and visceral fats.

Figure 12A:
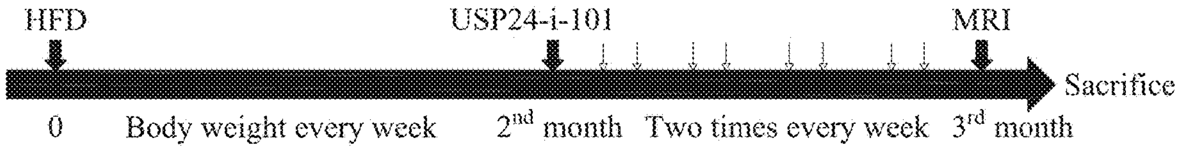
FIG. 12A shows the experimental flowchart for assessing the level and distribution of fat inside the HFD mice with or without USP24-i-101 treatment according to one embodiment of the present invention.
Figure 12B:
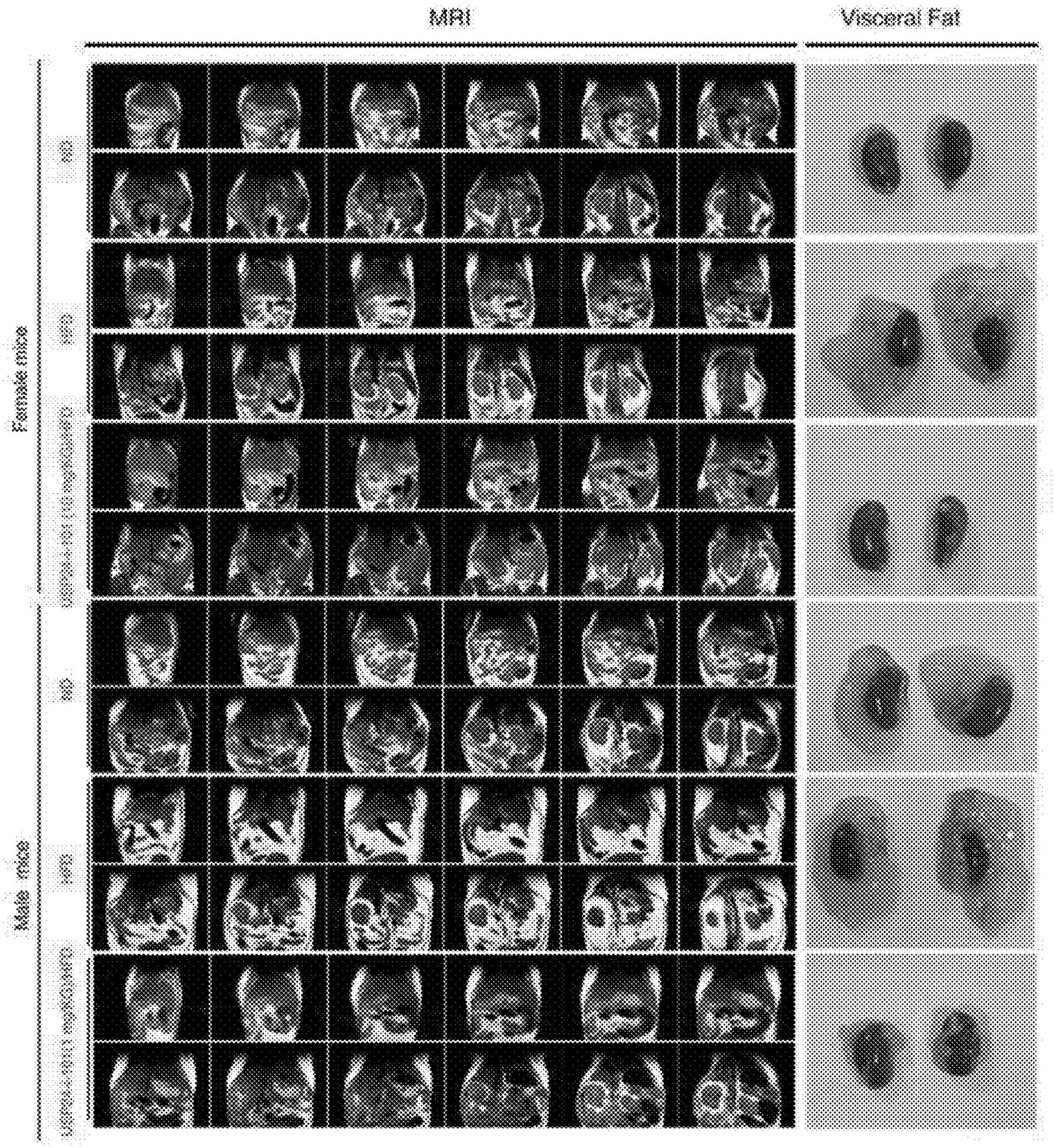
FIG. 12B shows magnetic resonance imaging (MRI) images and the gross appearance of visceral fats (kidneys) of HFD mice with or without USP24-i-101 treatment according to one embodiment of the present invention.

The HFD mice with or without USP24-i-101 treatment according to the experimental flowchart of FIG. 12A were examined by magnetic resonance imaging (MRI) equipment to assess the level and distribution of fat inside them. As shown in FIG. 12B, the results including the MRI in vivo signal and the collected kidney organs indicated that the signal of fat around subcutaneous and organs were dramatically accumulated in HFD mice but could be significantly inhibited after USP24-i-101 treatment.

Figure 13:
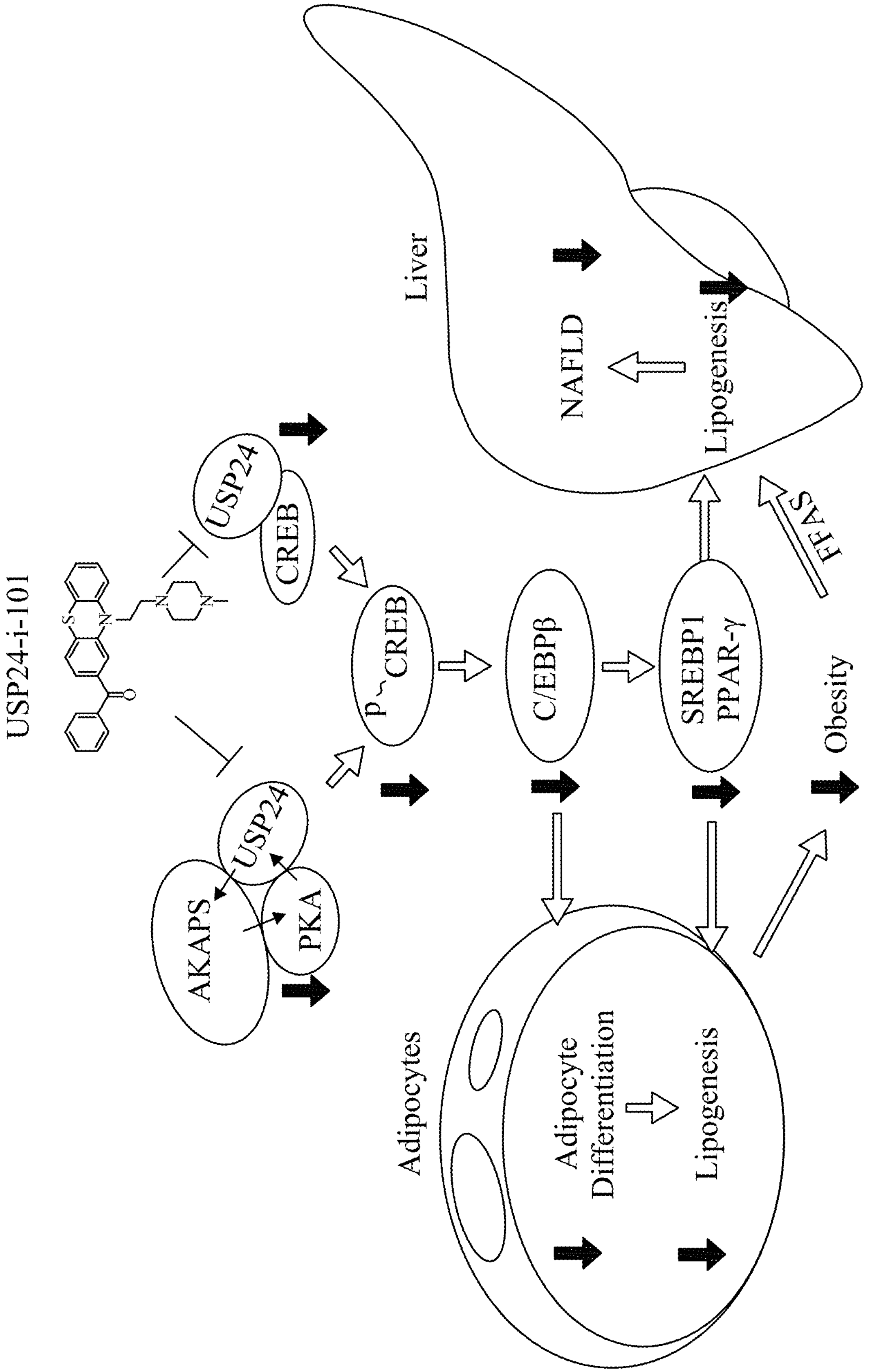
FIG. 13 illustrates the mechanism of the USP24 inhibitor involved in inhibiting lipogenesis according to one embodiment of the present invention.

Please referred to FIG. 13, which illustrated a possible mechanism of action of USP24 inhibitor according to an embodiment of the present invention. As shown in FIG. 13, PKA and USP24 positively regulation each other during lipogenesis phosphorylates CREB, thereby induces C/EBPb expression, subsequently induces PPARr expression, resulting SREBP1 expression, leading obesity and NAFLD. However, targeting USP24 by USP24-i-101 can significantly inhibit obesity and NAFLD, as shown in FIG. 13.

In summary, as demonstrated by the aforementioned in vitro cellular models, USP24 gene knockout mice, and high-fat diet animal models, it had been confirmed that USP24 inhibitor composition could effectively block lipogenesis, prevent lipid accumulation in the liver, reduce lipid droplets, lower the gene expression of PPAR-γ and PLIN1 in adipocytes, and improve liver activity. This ultimately led to a reduction in the formation of adipocytes, a decrease in lipid accumulation in the liver, and weight loss.

In conclusion, the specific compounds, specific patient groups, specific analysis models, or specific evaluation methods as aforementioned were only exemplary to describe the method of inhibiting lipogenesis with a ubiquitin-specific peptidase 24 (USP24) inhibitor. However, those skilled in the art of the present invention would readily understand that, within the spirit and scope of the present invention, other compounds, patient groups, analysis models, or evaluation methods could also be used for the purpose of the methods of inhibiting hepatic lipid accumulation and inhibiting the expression of PPAR-γ and/or PLIN1 genes with a USP 24 inhibitor composition and were not limited to those described above. For example, modifications of USP24-i compounds that did not alter their characteristics could be used to advantageously inhibit lipogenesis.

According to the embodiments of the present invention, the USP24 inhibitor composition comprises carbonyl-substituted phenyl compound, which can specifically inhibit lipogenesis in individuals with hyperlipidemia and hepatic lipid accumulation. It is further applicable for preparation of a pharmaceutical composition that inhibits lipogenesis.

Although the present invention has been described in considerable detail with reference to certain embodiments thereof, other embodiments are possible. Therefore, the spirit and scope of the appended claims should not be limited to the description of the embodiments contained herein.

What is claimed is:

1. A method of inhibiting lipogenesis with a ubiquitin-specific peptidase (USP) 24 inhibitor composition comprising administering the USP 24 inhibitor composition to a test subject that is a fat cell, pre-fat cell, and/or adipocyte-like cell, wherein the USP 24 inhibitor composition comprises a carbonyl-substituted phenyl compound and/or its salt as an active ingredient, as shown in formula (I):

(I)

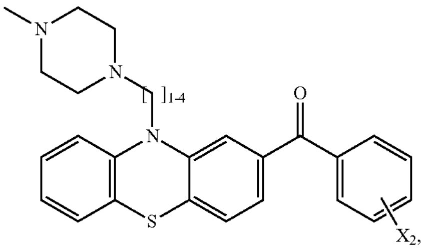

in formula (I), $X_2$ represents a hydrogen atom or a hydroxyl group, and the salt of said carbonyl-substituted phenyl compound is selected from a group consisting of oxalate, phosphate, sulfate, and hydrochloride.

2. The method according to claim 1, wherein the carbonyl-substituted phenyl compound has a structure as shown in either formula (I-3-1) or formula (I-3-3):

(I-3-1)

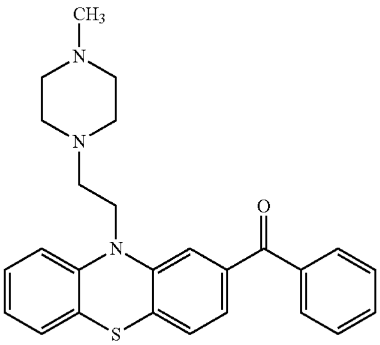

(I-3-3)

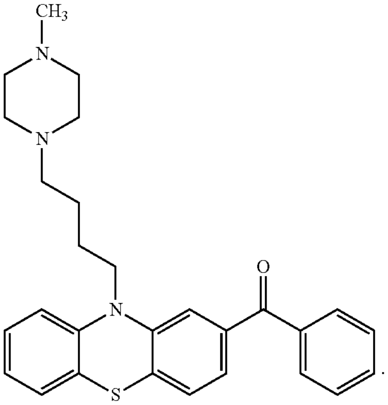

3. The method according to claim 1, wherein the USP 24 inhibitor composition further includes a pharmaceutically acceptable carrier.

4. The method according to claim 1, wherein the carbonyl-substituted phenyl compound is administered to the test subject in vitro at an effective dose of 1 μM to 20 μM.

5. A method of inhibiting hepatic lipid accumulation with a USP 24 inhibitor composition, wherein the USP 24 inhibitor composition comprises a carbonyl-substituted phenyl compound and/or its salt as an active ingredient, as shown in formula (I):

(I)

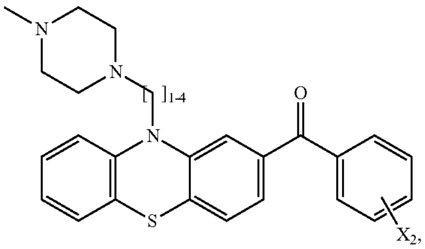

in formula (I), $X_2$ represents a hydrogen atom or a hydroxyl group, and the salt of said carbonyl-substituted phenyl compound is selected from a group consisting of oxalate, phosphate, sulfate, and hydrochloride, and wherein the carbonyl-substituted phenyl compound is administered to an individual having hyperlipidemia at an effective dose of 5 mg/kg body weight to 20 mg/kg body weight.

6. The method according to claim 5, wherein the individual is a mouse.

7. A method of inhibiting an expression levels of PPAR-γ and/or PLIN1 genes with a USP 24 inhibitor composition comprising administering the USP 24 inhibitor composition to a test subject, wherein the USP 24 inhibitor composition comprises a carbonyl-substituted phenyl compound and/or its salt as an active ingredient, as shown in formula (I-3-1):

(I-3-1)

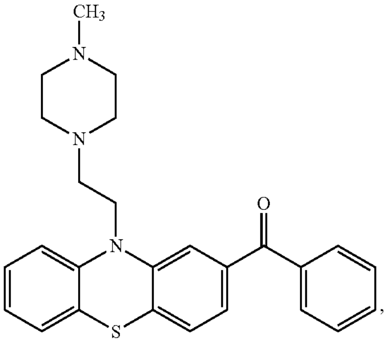

thereby reducing the expression levels of PPAR-γ and/or PLIN1 genes in the test subject, and the test subject is a fat cell, pre-fat cell, and/or adipocyte-like cell.

* * * * *